(12) United States Patent
Collins, Jr. et al.

(10) Patent No.: US 9,775,519 B2
(45) Date of Patent: Oct. 3, 2017

(54) NETWORK CONNECTIVITY UNIT FOR HOSPITAL BED

(71) Applicant: Hill-Rom Services, Inc., Batesville, IN (US)

(72) Inventors: Williams F. Collins, Jr., Columbus, IN (US); James M. Allen, Batesville, IN (US); Keith A. Huster, Sunman, IN (US); Carl W. Riley, Milan, IN (US); Patricia A. Glidewell, Cary, NC (US); Irvin J. Vanderpohl, III, Greensburg, IN (US); Richard J. Schuman, Cary, NC (US); Benjamin E. Howell, Fuquay-Varina, NC (US); Timothy D. Wildman, Metamora, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

(21) Appl. No.: 15/332,428

(22) Filed: Oct. 24, 2016

(65) Prior Publication Data
US 2017/0035295 A1    Feb. 9, 2017

Related U.S. Application Data

(63) Continuation of application No. 14/554,696, filed on Nov. 26, 2014, now Pat. No. 9,513,899, which is a (Continued)

(51) Int. Cl.
*G08B 5/22* (2006.01)
*A61B 5/00* (2006.01)
(Continued)

(52) U.S. Cl.
CPC .............. *A61B 5/002* (2013.01); *A61B 5/024* (2013.01); *A61B 5/1115* (2013.01); *A61B 5/1117* (2013.01); *A61B 5/447* (2013.01); *A61B 5/746* (2013.01); *A61G 7/018* (2013.01); *A61G 12/00* (2013.01); *G06F 8/65* (2013.01); *G06F 19/327* (2013.01); *G06F 19/3412* (2013.01); *G06F 19/3418* (2013.01); *G07C 3/00* (2013.01);
(Continued)

(58) Field of Classification Search
CPC .......... G08B 21/02; G06F 8/65; A61B 5/447; A61G 7/018
USPC ....... 340/286.07, 3.1, 517, 521, 539.12, 506
See application file for complete search history.

(56) References Cited

U.S. PATENT DOCUMENTS

| 2,330,356 A | 9/1943 | Belliveau |
| 2,335,524 A | 11/1943 | Lomax |

(Continued)

FOREIGN PATENT DOCUMENTS

| WO | WO 02/091297 A1 | 11/2002 |
| WO | WO 2004/036390 A2 | 4/2004 |

*Primary Examiner* — Daryl Pope
(74) *Attorney, Agent, or Firm* — Barnes & Thornburg LLP

(57) ABSTRACT

A hospital bed is programmable with new firmware that is downloaded to the bed over a network. The firmware is downloaded to the bed automatically from a remote computer device. The remote computer device receives a message from the hospital bed which includes data regarding the version number of the bed's current firmware, and if the version number indicates that the firmware is an outdated version, the remote computer device downloads a new version of the firmware to the bed.

20 Claims, 16 Drawing Sheets

Related U.S. Application Data continuation of application No. 14/098,937, filed on Dec. 6, 2013, now Pat. No. 8,917,166, which is a continuation of application No. 13/629,708, filed on Sep. 28, 2012, now Pat. No. 8,604,917, which is a continuation of application No. 12/959,486, filed on Dec. 3, 2010, now Pat. No. 8,284,047, which is a continuation of application No. 11/672,367, filed on Feb. 7, 2007, now Pat. No. 7,852,208, which is a continuation-in-part of application No. 11/189,781, filed on Jul. 27, 2005, now Pat. No. 7,319,386.

(60) Provisional application No. 60/773,286, filed on Feb. 13, 2006, provisional application No. 60/652,699, filed on Feb. 14, 2005, provisional application No. 60/642,692, filed on Jan. 10, 2005, provisional application No. 60/598,045, filed on Aug. 2, 2004.

(51) Int. Cl.
*A61B 5/11* (2006.01)
*A61G 7/018* (2006.01)
*G06F 19/00* (2011.01)
*G07C 3/00* (2006.01)
*G08B 21/22* (2006.01)
*G06F 9/445* (2006.01)
*H04L 29/08* (2006.01)
*A61B 5/024* (2006.01)
*A61G 12/00* (2006.01)

(52) U.S. Cl.
CPC .............. *G08B 5/22* (2013.01); *G08B 5/222* (2013.01); *G08B 21/22* (2013.01); *H04L 67/10* (2013.01)

(56) References Cited

U.S. PATENT DOCUMENTS

| | | |
|---|---|---|
| 2,736,888 A | 2/1956 | McLain |
| 2,896,021 A | 7/1959 | Philipps |
| 3,098,220 A | 7/1963 | De Graaf |
| 3,439,320 A | 4/1969 | Ward |
| 3,478,344 A | 11/1969 | Schwitzgebel et al. |
| 3,553,383 A | 1/1971 | Rochtus |
| 3,599,199 A | 8/1971 | Bunting |
| 3,599,200 A | 8/1971 | Bunting |
| 3,696,384 A | 10/1972 | Lester |
| 3,739,329 A | 6/1973 | Lester |
| 3,767,859 A | 10/1973 | Doering et al. |
| 3,805,265 A | 4/1974 | Lester |
| 3,913,153 A | 10/1975 | Adams et al. |
| 3,973,200 A | 8/1976 | Akerberg |
| 4,067,005 A | 1/1978 | Levy et al. |
| 4,150,284 A | 4/1979 | Trenkler et al. |
| 4,151,407 A | 4/1979 | McBride et al. |
| 4,183,015 A | 1/1980 | Drew et al. |
| 4,216,462 A | 8/1980 | McGrath et al. |
| 4,225,953 A | 9/1980 | Simon et al. |
| 4,228,426 A | 10/1980 | Roberts |
| 4,237,344 A | 12/1980 | Moore |
| 4,264,982 A | 4/1981 | Sakarya |
| 4,275,385 A | 6/1981 | White |
| 4,279,433 A | 7/1981 | Petaja |
| 4,298,863 A | 11/1981 | Natitus et al. |
| 4,331,953 A | 5/1982 | Blevins et al. |
| 4,356,475 A | 10/1982 | Neumann et al. |
| 4,418,334 A | 11/1983 | Burnett |
| 4,455,548 A | 6/1984 | Burnett |
| 4,489,387 A | 12/1984 | Lamb et al. |
| 4,495,495 A | 1/1985 | Ormanns et al. |
| 4,495,496 A | 1/1985 | Miller, III |
| 4,539,560 A | 9/1985 | Fleck et al. |
| 4,577,185 A | 3/1986 | Andersen |
| 4,578,671 A | 3/1986 | Flowers |
| 4,593,273 A | 6/1986 | Narcisse |
| 4,598,275 A | 7/1986 | Ross et al. |
| 4,601,064 A | 7/1986 | Shipley |
| 4,649,385 A | 3/1987 | Aires et al. |
| 4,680,790 A | 7/1987 | Packard et al. |
| 4,709,330 A | 11/1987 | Yokoi et al. |
| 4,740,788 A | 4/1988 | Konneker |
| 4,752,951 A | 6/1988 | Konneker |
| 4,792,798 A | 12/1988 | Wilowski |
| 4,795,905 A | 1/1989 | Zierhut |
| 4,814,751 A | 3/1989 | Hawkins et al. |
| 4,833,452 A | 5/1989 | Currier |
| 4,833,467 A | 5/1989 | Kobayashi et al. |
| 4,837,568 A | 6/1989 | Snaper |
| 4,853,692 A | 8/1989 | Wolk et al. |
| 4,899,135 A | 2/1990 | Ghahariiran |
| 4,947,152 A | 8/1990 | Hodges |
| 4,955,000 A | 9/1990 | Nastrom |
| 4,967,195 A | 10/1990 | Shipley |
| 4,990,892 A | 2/1991 | Guest et al. |
| 4,998,095 A | 3/1991 | Shields |
| 4,998,939 A | 3/1991 | Potthast et al. |
| 5,006,830 A | 4/1991 | Merritt |
| 5,027,314 A | 6/1991 | Linwood et al. |
| 5,041,086 A | 8/1991 | Koenig et al. |
| 5,062,151 A | 10/1991 | Shipley |
| 5,065,154 A | 11/1991 | Kaiser |
| 5,086,290 A | 2/1992 | Murray et al. |
| 5,103,108 A | 4/1992 | Crimmins |
| 5,124,991 A | 6/1992 | Allen |
| 5,137,033 A | 8/1992 | Norton |
| 5,153,584 A | 10/1992 | Engira |
| 5,266,944 A | 11/1993 | Carroll et al. |
| 5,291,399 A | 3/1994 | Chaco |
| 5,319,355 A | 6/1994 | Russek |
| 5,319,363 A | 6/1994 | Welch et al. |
| 5,357,254 A | 10/1994 | Kah, Jr. |
| 5,375,604 A | 12/1994 | Kelly et al. |
| 5,396,224 A | 3/1995 | Dukes et al. |
| 5,396,227 A | 3/1995 | Carroll et al. |
| 5,416,695 A | 5/1995 | Stutman et al. |
| 5,434,775 A | 7/1995 | Sims et al. |
| 5,446,678 A | 8/1995 | Saltzstein et al. |
| 5,455,560 A | 10/1995 | Owen |
| 5,458,123 A | 10/1995 | Unger |
| 5,461,390 A | 10/1995 | Hoshen |
| 5,475,367 A | 12/1995 | Prevost |
| 5,534,851 A | 7/1996 | Russek |
| 5,537,459 A | 7/1996 | Price et al. |
| 5,548,637 A | 8/1996 | Heller et al. |
| 5,549,113 A | 8/1996 | Halleck et al. |
| 5,561,412 A | 10/1996 | Novak et al. |
| 5,568,119 A | 10/1996 | Schipper et al. |
| 5,576,952 A | 11/1996 | Stutman et al. |
| 5,579,001 A | 11/1996 | Dempsey et al. |
| 5,588,005 A | 12/1996 | Ali et al. |
| 5,594,786 A | 1/1997 | Chaco et al. |
| 5,621,388 A | 4/1997 | Sherburne et al. |
| 5,635,907 A | 6/1997 | Bernard et al. |
| 5,636,245 A | 6/1997 | Ernst et al. |
| 5,640,953 A | 6/1997 | Bishop et al. |
| 5,650,769 A | 7/1997 | Campana, Jr. |
| 5,650,770 A | 7/1997 | Schlager et al. |
| 5,664,270 A | 9/1997 | Bell et al. |
| 5,682,139 A | 10/1997 | Pradeep et al. |
| 5,686,888 A | 11/1997 | Welles, II |
| 5,686,902 A | 11/1997 | Reis et al. |
| 5,687,734 A | 11/1997 | Dempsey et al. |
| 5,689,229 A | 11/1997 | Chaco et al. |
| 5,691,980 A | 11/1997 | Welles, II et al. |
| 5,699,038 A | 12/1997 | Ulrich et al. |
| 5,705,980 A | 1/1998 | Shapiro |
| 5,708,421 A | 1/1998 | Boyd |
| 5,713,856 A | 2/1998 | Eggers et al. |
| 5,719,761 A | 2/1998 | Gatti et al. |
| 5,731,757 A | 3/1998 | Layson, Jr. |
| 5,742,237 A | 4/1998 | Bledsoe |
| 5,751,246 A | 5/1998 | Hertel |

(56) References Cited

U.S. PATENT DOCUMENTS

| | | |
|---|---|---|
| 5,752,917 A | 5/1998 | Fuchs |
| 5,760,704 A | 6/1998 | Barton et al. |
| 5,767,791 A | 6/1998 | Stoop et al. |
| 5,781,442 A | 7/1998 | Engleson et al. |
| 5,793,290 A | 8/1998 | Eagleson et al. |
| 5,808,564 A | 9/1998 | Simms et al. |
| 5,812,056 A | 9/1998 | Law |
| 5,822,418 A | 10/1998 | Yacenda et al. |
| 5,822,544 A | 10/1998 | Chaco et al. |
| 5,838,223 A | 11/1998 | Gallant et al. |
| 5,844,488 A | 12/1998 | Musick |
| 5,867,821 A | 2/1999 | Ballantyne et al. |
| 5,877,675 A | 3/1999 | Rebstock et al. |
| 5,933,488 A | 8/1999 | Marcus et al. |
| 5,936,539 A | 8/1999 | Fuchs |
| 5,942,986 A | 8/1999 | Shabot et al. |
| 5,944,659 A | 8/1999 | Flach et al. |
| 5,963,137 A | 10/1999 | Waters, Sr. |
| 5,974,389 A | 10/1999 | Clark et al. |
| 5,991,728 A | 11/1999 | DeBusk et al. |
| 5,995,937 A | 11/1999 | DeBusk et al. |
| 6,014,633 A | 1/2000 | DeBusk et al. |
| 6,057,758 A | 5/2000 | Dempsey et al. |
| 6,057,782 A | 5/2000 | Koenig |
| 6,067,019 A | 5/2000 | Scott |
| 6,076,166 A | 6/2000 | Moshfeghi et al. |
| 6,078,261 A | 6/2000 | Davsko |
| 6,085,493 A | 7/2000 | DeBusk et al. |
| 6,088,362 A | 7/2000 | Turnbull et al. |
| 6,093,146 A | 7/2000 | Filangeri |
| 6,097,308 A | 8/2000 | Albert et al. |
| 6,111,509 A | 8/2000 | Holmes |
| 6,125,350 A | 9/2000 | Dirbas |
| 6,133,837 A | 10/2000 | Riley |
| 6,147,592 A | 11/2000 | Ulrich et al. |
| 6,183,417 B1 | 2/2001 | Geheb et al. |
| 6,208,250 B1 | 3/2001 | Dixon et al. |
| 6,241,668 B1 | 6/2001 | Herzog |
| 6,259,355 B1 | 7/2001 | Chaco et al. |
| 6,264,614 B1 | 7/2001 | Albert et al. |
| 6,272,347 B1 | 8/2001 | Griffith et al. |
| 6,279,183 B1 | 8/2001 | Kummer et al. |
| 6,287,253 B1 | 9/2001 | Ortega et al. |
| 6,302,844 B1 | 10/2001 | Walker et al. |
| 6,314,556 B1 | 11/2001 | DeBusk et al. |
| 6,320,510 B2 | 11/2001 | Menkedick et al. |
| 6,344,794 B1 | 2/2002 | Ulrich et al. |
| 6,348,777 B1 | 2/2002 | Brown et al. |
| 6,362,725 B1 | 3/2002 | Ulrich et al. |
| 6,364,834 B1 | 4/2002 | Reuss et al. |
| 6,398,727 B1 | 6/2002 | Bui et al. |
| 6,406,426 B1 | 6/2002 | Reuss et al. |
| 6,407,335 B1 | 6/2002 | Franklin-Lees et al. |
| 6,412,980 B1 | 7/2002 | Lounsberry et al. |
| 6,416,471 B1 | 7/2002 | Kumar et al. |
| 6,421,649 B1 | 7/2002 | Rattner |
| 6,439,769 B1 | 8/2002 | Polkus et al. |
| 6,441,742 B1 | 8/2002 | Lovely et al. |
| 6,442,290 B1 | 8/2002 | Ellis et al. |
| 6,445,299 B1 | 9/2002 | Rojas, Jr. |
| 6,450,956 B1 | 9/2002 | Rappaport et al. |
| 6,462,656 B2 | 10/2002 | Ulrich et al. |
| 6,486,792 B1 | 11/2002 | Moster et al. |
| 6,493,568 B1 | 12/2002 | Bell et al. |
| 6,494,831 B1 | 12/2002 | Koritzinsky |
| 6,510,344 B1 | 1/2003 | Halpern |
| 6,516,324 B1 | 2/2003 | Jones et al. |
| 6,526,310 B1 | 2/2003 | Carter et al. |
| 6,529,164 B1 | 3/2003 | Carter |
| 6,533,453 B1 | 3/2003 | Heidsieck et al. |
| 6,535,576 B2 | 3/2003 | Vafi et al. |
| 6,539,393 B1 | 3/2003 | Kabala |
| 6,544,173 B2 | 4/2003 | West et al. |
| 6,544,174 B2 | 4/2003 | West et al. |
| 6,551,243 B2 | 4/2003 | Bocionek et al. |
| 6,553,106 B1 | 4/2003 | Gould et al. |
| 6,554,174 B1 | 4/2003 | Aceves |
| 6,556,630 B1 | 4/2003 | Brinsfield et al. |
| 6,560,274 B1 | 5/2003 | Leitgeb et al. |
| 6,572,556 B2 | 6/2003 | Stoycos et al. |
| 6,575,901 B2 | 6/2003 | Stoycos et al. |
| 6,581,204 B2 | 6/2003 | DeBusk et al. |
| 6,584,182 B2 | 6/2003 | Brodnick |
| 6,584,454 B1 | 6/2003 | Hummel, Jr. et al. |
| 6,585,645 B2 | 7/2003 | Hutchinson |
| 6,589,170 B1 | 7/2003 | Flach et al. |
| 6,593,528 B2 | 7/2003 | Franklin-Lees et al. |
| 6,594,146 B2 | 7/2003 | Frangesch et al. |
| 6,594,519 B2 | 7/2003 | Stoycos et al. |
| 6,600,421 B2 | 7/2003 | Freeman |
| 6,603,494 B1 | 8/2003 | Banks et al. |
| 6,609,115 B1 | 8/2003 | Mehring et al. |
| 6,616,606 B1 | 9/2003 | Petersen et al. |
| 6,622,088 B2 | 9/2003 | Hood |
| 6,640,246 B1 | 10/2003 | Gary, Jr. et al. |
| 6,643,238 B2 | 11/2003 | Nakajima |
| 6,650,346 B1 | 11/2003 | Jaeger et al. |
| 6,659,947 B1 | 12/2003 | Carter et al. |
| 6,665,385 B2 | 12/2003 | Rogers et al. |
| 6,665,820 B1 | 12/2003 | Frowein et al. |
| 6,669,630 B1 | 12/2003 | Joliat et al. |
| 6,671,547 B2 | 12/2003 | Lyster et al. |
| 6,671,563 B1 | 12/2003 | Engelson et al. |
| 6,685,633 B2 | 2/2004 | Albert et al. |
| 6,689,091 B2 | 2/2004 | Bui et al. |
| 6,694,367 B1 | 2/2004 | Miesbauer et al. |
| 6,694,509 B1 | 2/2004 | Stoval et al. |
| 6,697,765 B2 | 2/2004 | Kuth |
| 6,707,476 B1 | 3/2004 | Hochstedler |
| 6,714,913 B2 | 3/2004 | Brandt et al. |
| 6,721,818 B1 | 4/2004 | Nakamura |
| 6,726,634 B2 | 4/2004 | Freeman |
| 6,727,818 B1 | 4/2004 | Wildman et al. |
| 6,731,311 B2 | 5/2004 | Bufe et al. |
| 6,731,989 B2 | 5/2004 | Engleson et al. |
| 6,740,033 B1 | 5/2004 | Olejniczak et al. |
| 6,749,566 B2 | 6/2004 | Russ |
| 6,751,630 B1 | 6/2004 | Franks et al. |
| 6,754,545 B2 | 6/2004 | Haeuser et al. |
| 6,754,883 B2 | 6/2004 | DeBusk et al. |
| 6,759,959 B2 | 7/2004 | Wildman |
| 6,763,541 B2 | 7/2004 | Mahoney et al. |
| 6,771,172 B1 | 8/2004 | Robinson et al. |
| 6,773,396 B2 | 8/2004 | Flach et al. |
| 6,778,225 B2 | 8/2004 | David |
| 6,781,517 B2 | 8/2004 | Moster et al. |
| 6,784,797 B2 | 8/2004 | Smith et al. |
| 6,791,460 B2 | 9/2004 | Dixon et al. |
| 6,792,396 B2 | 9/2004 | Inda et al. |
| 6,801,227 B2 | 10/2004 | Bocionek et al. |
| 6,807,543 B2 | 10/2004 | Muthya |
| 6,825,763 B2 | 11/2004 | Ulrich et al. |
| 6,826,578 B2 | 11/2004 | Brackett et al. |
| 6,828,992 B1 | 12/2004 | Freeman et al. |
| 6,829,796 B2 | 12/2004 | Salvatini et al. |
| 6,830,549 B2 | 12/2004 | Bui et al. |
| 6,832,199 B1 | 12/2004 | Kucek et al. |
| 6,840,117 B2 | 1/2005 | Hubbard, Jr. |
| 6,847,814 B1 | 1/2005 | Vogeleisen |
| 6,868,256 B2 | 3/2005 | Dooley et al. |
| 6,871,211 B2 | 3/2005 | Labounty et al. |
| 6,873,884 B2 | 3/2005 | Brackett et al. |
| 6,876,303 B2 | 4/2005 | Reeder et al. |
| 6,876,985 B2 | 4/2005 | Kawanaka |
| 6,885,288 B2 | 4/2005 | Pincus |
| 6,891,909 B2 | 5/2005 | Hurley et al. |
| 6,904,161 B1 | 6/2005 | Becker et al. |
| 6,909,995 B2 | 6/2005 | Shiraishi |
| 6,912,549 B2 | 6/2005 | Rotter et al. |
| 6,915,170 B2 | 7/2005 | Engleson et al. |
| 6,925,367 B2 | 8/2005 | Fontius |
| 6,930,878 B2 | 8/2005 | Brackett et al. |
| 6,958,706 B2 | 10/2005 | Chaco et al. |
| 7,068,143 B2 | 6/2006 | Doering et al. |

(56) References Cited

U.S. PATENT DOCUMENTS

| | | |
|---|---|---|
| 7,092,376 B2 | 8/2006 | Schuman |
| 7,138,902 B2 | 11/2006 | Menard |
| 7,290,451 B2 | 11/2007 | Taniguchi et al. |
| 7,292,135 B2 | 11/2007 | Bixler et al. |
| 7,319,386 B2 | 1/2008 | Collins, Jr. et al. |
| 7,333,002 B2 | 2/2008 | Bixler et al. |
| 7,746,218 B2 | 6/2010 | Collins, Jr. et al. |
| 7,852,208 B2 | 12/2010 | Collins, Jr. et al. |
| 8,284,047 B2 | 10/2012 | Collins, Jr. et al. |
| 8,604,917 B2 * | 12/2013 | Collins ............... A61B 5/447 340/286.07 |
| 8,917,166 B2 | 12/2014 | Collins, Jr. et al. |
| 9,513,899 B2 | 12/2016 | Collins, Jr. et al. |
| 2001/0050610 A1 | 12/2001 | Gelston |
| 2001/0051765 A1 | 12/2001 | Walker et al. |
| 2002/0014951 A1 | 2/2002 | Kramer et al. |
| 2002/0044043 A1 | 4/2002 | Chaco et al. |
| 2002/0044059 A1 | 4/2002 | Reeder et al. |
| 2002/0067273 A1 | 6/2002 | Jaques et al. |
| 2002/0070867 A1 | 6/2002 | Conway et al. |
| 2002/0080037 A1 | 6/2002 | Dixon et al. |
| 2002/0103674 A1 | 8/2002 | Reeder et al. |
| 2002/0151990 A1 | 10/2002 | Ulrich et al. |
| 2002/0173991 A1 | 11/2002 | Avitall |
| 2002/0186136 A1 | 12/2002 | Schuman |
| 2002/0196141 A1 | 12/2002 | Boone et al. |
| 2003/0010345 A1 | 1/2003 | Koblasz et al. |
| 2003/0028449 A1 | 2/2003 | Heinen et al. |
| 2003/0030569 A1 | 2/2003 | Ulrich et al. |
| 2003/0052787 A1 | 3/2003 | Zerhusen et al. |
| 2003/0074222 A1 | 4/2003 | Rosow et al. |
| 2003/0146835 A1 | 8/2003 | Carter |
| 2003/0149598 A1 | 8/2003 | Santoso et al. |
| 2003/0176798 A1 | 9/2003 | Simon |
| 2003/0206116 A1 | 11/2003 | Weiner et al. |
| 2004/0183681 A1 | 9/2004 | Smith |
| 2004/0183684 A1 | 9/2004 | Callaway |
| 2004/0186358 A1 | 9/2004 | Chernow et al. |
| 2004/0193449 A1 | 9/2004 | Wildman et al. |
| 2004/0236218 A1 | 11/2004 | Taniguchi et al. |
| 2005/0035862 A1 | 2/2005 | Wildman et al. |
| 2005/0219059 A1 | 10/2005 | Ulrich et al. |
| 2005/0242946 A1 | 11/2005 | Hubbard, Jr. et al. |
| 2006/0049936 A1 | 3/2006 | Collins, Jr. et al. |
| 2006/0248221 A1 | 11/2006 | Hottel et al. |
| 2006/0279427 A1 | 12/2006 | Becker et al. |
| 2007/0210917 A1 | 9/2007 | Collins, Jr. et al. |
| 2008/0094207 A1 | 4/2008 | Collins, Jr. et al. |
| 2011/0074571 A1 | 3/2011 | Collins, Jr. et al. |
| 2013/0021143 A1 | 1/2013 | Collins et al. |
| 2014/0091913 A1 | 4/2014 | Collins, Jr. et al. |
| 2015/0082295 A1 | 3/2015 | Collins, Jr. et al. |

* cited by examiner

NETWORK CONNECTIVITY UNIT FOR HOSPITAL BED

CROSS-REFERENCE TO RELATED APPLICATIONS

This application is a continuation of U.S. application Ser. No. 14/554,696, filed Nov. 26, 2014, which issued as U.S. Pat. No. 9,513,899, which is a continuation of U.S. application Ser. No. 14/098,937, filed Dec. 6, 2013, which issued as U.S. Pat. No. 8,917,166, which is a continuation of U.S. application Ser. No. 13/629,708, filed Sep. 28, 2012, which issued as U.S. Pat. No. 8,604,917 on Dec. 10, 2013, which is a continuation of U.S. application Ser. No. 12/959,486, filed Dec. 3, 2010, which issued as U.S. Pat. No. 8,284,047 on Oct. 9, 2012, and which is a continuation of U.S. application Ser. No. 11/672,367, filed Feb. 7, 2007, which issued as U.S. Pat. No. 7,852,208 on Dec. 14, 2010, each of which is hereby incorporated by reference herein and which claimed the benefit, under 35 U.S.C. §119(e), of U.S. Provisional Application No. 60/773,286 which was filed Feb. 13, 2006 and which is hereby incorporated by reference herein; and U.S. application Ser. No. 11/672,367 also claimed priority as a continuation-in-part of U.S. patent application Ser. No. 11/189,781, which was filed on Jul. 27, 2005 and which claimed the benefit, under 35 U.S.C. §119(e), of U.S. Provisional Patent Application Ser. No. 60/652,699 filed Feb. 14, 2005; of U.S. Provisional Patent Application Ser. No. 60/642,692 filed Jan. 10, 2005; and of U.S. Provisional Patent Application Ser. No. 60/598,045 filed Aug. 2, 2004; each of which is hereby incorporated by reference herein in its entirety.

BACKGROUND OF THE INVENTION

The present disclosure relates to hospital beds and particularly, to data communication from hospital beds to other devices in a healthcare facility. More particularly, the present disclosure relates to data communication from hospital beds to remote computer devices and/or to portable wireless communication devices carried by caregivers.

Some hospital beds are configured to communicate information to a nurse call system. Such nurse call systems typically have a computer at a remote nurse's station with a display on which information concerning bed status is shown. One or more nurse call buttons are sometimes provided on a hospital bed, such as on one or more siderails of the bed and/or on a handheld pendant that is coupled to the bed. A patient may press one of the nurse call buttons to request to speak with a nurse. A nurse at the remote nurse's station and the patient may communicate with each other over a two-way communications link which includes audio circuitry, such as a microphone and a speaker included on the bed or mounted on a room wall near the bed. In addition, the nurse at the remote nurse's station may use the computer to establish a two-way communications link between the remote nurse's station and a caregiver at some other location in a healthcare facility and/or between the patient placing the nurse call and a caregiver at some other location in the healthcare facility. See, for example, U.S. Pat. Nos. 5,561,412 and 5,699,038.

Hospital beds that connect to nurse call systems, typically do so via a wired connection established by a nurse call cable that extends between the bed and an interface unit having a jack mounted on a wall or headwall unit in the hospital room in which the bed is situated. Typically, a power cord from the bed also plugs into a power outlet on the wall or headwall unit. Before the bed is moved from one location to another in a healthcare facility, the nurse call cable and the power cord need to be unplugged. Caregivers sometimes forget to unplug the nurse call cable resulting in damage to the nurse call cable when the bed is wheeled away from the wall. When the bed arrives at its new location, the caregivers need to remember to plug in both the power cord and the nurse call cable. When the nurse call cable is unplugged, bed status data is no longer communicated to the nurse call system. In addition, many prior art nurse call systems are configured as local area networks (LAN's) which require the installation in the healthcare facility of the associated LAN infrastructure, such as the bed interface units and the wiring from the bed interface units to the computer at the remote nurse's station.

SUMMARY OF THE INVENTION

The present invention comprises a system, apparatus and/or method that has one or more of the following features and/or steps, which alone or in any combination may comprise patentable subject matter:

A hospital bed may have wireless communication circuitry. The wireless communication circuitry may be operable to transmit bed status data wirelessly to a network and to receive messages wirelessly from the network. The wireless communication circuitry may also be operable to transmit bed location data wirelessly to the network to indicate a location in a healthcare facility at which the hospital bed is located. The bed location data may comprise data received from a unit mounted to a wall in a room of the healthcare facility. The wireless communication circuitry may be operable to transmit housekeeping data wirelessly to the network to indicate that the hospital bed needs to be cleaned. The housekeeping data may be transmitted in response to a person pressing a button on the hospital bed.

The wireless communication circuitry may be operable to transmit patient weight data wirelessly to the network. The patient weight data may be transmitted wirelessly in response to a query initiated by a caregiver at a remote computer. The wireless communication circuitry may be operable to transmit patient position mode data wirelessly to the network. The patient position mode data may be indicative of which of a plurality of modes a patient position monitor of the hospital bed is operating. A first mode of the patient position monitor of the bed may be a movement mode in which patient movement of a first amount is detected. A second mode of the patient position monitor of the bed may be an egress mode in which patient movement of a second amount greater than the first amount is detected. A third mode of the patient position monitor may be an exit mode in which patient movement of a third amount greater than the second amount is detected. The wireless communication circuitry may be operable to transmit alarm data wirelessly to the network to indicate that a condition associated with the selected patient position mode has been violated.

The bed status data may include lockout data to indicate that at least one bed motor has been locked out by a caregiver such that a patient is unable to operate the motor using one or more bed controls. The bed status data may include turn assist data to indicate whether a turn assist feature of a mattress of the hospital bed is being used. The bed status data may include max inflate data to indicate whether a max inflate feature of a mattress of the hospital bed is being used. The bed status data may include heel suspension data to indicate whether a heel suspension mode of a mattress of the hospital bed is being used.

The bed status data may include surface therapy data transmitted wirelessly to the network to indicate whether a surface therapy feature of a mattress of the hospital bed is being used. The surface therapy data may indicate whether at least one of the following surface therapies is being used: low air loss, continuous lateral rotation, alternating pressure, sequential pressure, percussion, and vibration. The surface therapy data may indicate a parameter, such as pressure, time, frequency, angle of rotation, percentage of rotation, flow rate, and the like, associated with the surface therapy. The surface therapy data may indicate that an alarm condition, such as loss of pressure or an interruption in the associated therapy, is occurring.

The bed status data may include battery data to indicate a status of a battery of the hospital bed. The battery data may indicate at least one of the following: that the battery is present on the bed, that the battery is absent from the bed, that the battery is fully charged, and that the battery needs charging. The bed status data may include AC power data to indicate whether the hospital bed is connected to AC power. The bed status data may includes service data to indicate that the hospital bed needs to be serviced. The bed status data may include CPR release data to indicate that a CPR release handle of the hospital bed has been activated to rapidly lower a head section of the bed. The bed status data may include head angle data to indicate an angle at which a head section of the hospital bed is inclined. The head angle data may indicate the angle at which the head section of the hospital bed is inclined relative to some other portion of the hospital bed, relative to horizontal, or relative to vertical.

The hospital bed may have an indicator to indicate whether the hospital bed has established wireless communications with the network. The hospital bed may have an indicator to indicate whether a template of alarm conditions has been set up for the hospital bed at a remote computer device coupled to the network. One or both of the indicator to indicate that wireless communications have been established and the indicator to indicate that an alarm condition template has been set up may comprise a light emitting diode on a siderail or on a base frame of the bed. The hospital bed may have a button that is pressed to suspend the template of alarm conditions at the remote computer device so that changes in bed status do not result in alarm messages at the remoter computer device and/or at portable wireless communication devices carried by caregivers.

The hospital bed may be programmable with new firmware that is downloaded to the bed. The firmware may be downloaded to the bed automatically from a remote computer device. The remote computer device may receive a message from the hospital bed which includes data regarding the version number of the bed's current firmware, and if the version number indicates that the firmware is an outdated version, the remote computer device may download a new version of the firmware to the bed. The firmware may be downloaded to the bed according to a file transfer protocol (FTP). The wireless communication circuitry may be operable to transmit a message in which is embedded an IP address associated with a remote computer to which the message is destined. The wireless communication circuitry may be operable to transmit a message in which is embedded an IP address and/or a MAC address associated with the hospital bed.

The wireless communication circuitry may be operable to transmit an XML message. The wireless communication circuitry may be operable to convert the XML message into ASCII format prior to transmission. The wireless communication circuitry may be operable to transmit a message to a preprogrammed e-mail address in response to a preprogrammed event occurring on the hospital bed. The wireless communication circuitry may be operable to transmit a heartbeat signal. The heartbeat signal may includes a copyright notice. The copyright notice may comprise a company name and a year. The heartbeat signal may be transmitted at least once per minute. The wireless communication circuitry may be configured to resend the heartbeat signal if a heartbeat received message is not received by the hospital bed within a predetermined period of time that is less than one minute.

The wireless communication circuitry may be operable to transmit configuration data to indicate the capabilities of the hospital bed. The hospital bed may have a TCP/IP port to which at least one other device is couplable and the wireless communication circuitry of the hospital bed may be operable to transmit wirelessly device data received from the at least one other device. The wireless communication circuitry may be operable to transmit wirelessly according to the 802.11b or 802.11g protocol.

According to this disclosure, a system for use with a network of computer devices in a healthcare facility may comprise a hospital bed having first wireless communication circuitry operable to transmit bed status data wirelessly to the network and a surface supported by the hospital bed. The surface may have second wireless communication circuitry operable to transmit surface status data wirelessly to the network. The second wireless communication circuitry may be operable independent of the first wireless communication circuitry.

A frequency at which the first wireless communication circuitry transmits may be different than a frequency at which the second wireless communication circuitry transmits. The first and second wireless communication circuitry may transmit wirelessly according to the 802.11b or 802.11g protocol.

The system may include a computer device coupled to the network remotely from the hospital bed and the surface. The computer device may be operable to receive the bed status data and to transmit a control message to the surface in response to the bed status data received from the hospital bed. For example, if the bed status data indicates that a CPR release handle of the bed has been pulled, then the control message to the surface may result in the surface going into a max inflate mode to harden the mattress in preparation for CPR to be performed on the patient or, alternatively, the control message may result in the surface completely deflating so that the patient is supported on underlying bed sections in preparation for CPR to be performed on the patient. As another example, if the bed status data indicates that casters of the hospital bed have been unbraked, then the command message to the surface may indicate that a therapy, such as lateral rotation therapy, alternating pressure therapy, percussion therapy, etc. should be stopped in preparation for the bed being moved to a new location.

The computer device may be operable to receive the surface status data and to transmit a control message to the hospital bed in response to the surface status data received from the surface. For example, if the surface status data indicates that lateral rotation therapy is active, then the control message to the hospital bed may lock out a head section motor to prevent the head section from being raised during the lateral rotation therapy.

Also according to this disclosure, a system for use with a network of computer devices in a healthcare facility may comprise a hospital bed having communication circuitry operable to transmit messages to the network and a workflow computer system coupled to the network. The workflow computer system may be operable to assign tasks to staff members. At least one task assigned to at least one of the staff members may be assigned by the workflow computer system in response to receipt of a message transmitted from the communication circuitry of the hospital bed over the network.

The at least one task assigned to at least one of the staff members in response to the message may comprise a housekeeping task or a bed service task. The housekeeping task may comprise cleaning the hospital bed. The message transmitted from the communication circuit may comprise a wireless message. The hospital bed automatically may transmit the message in response to a sensed condition of the hospital bed. The hospital bed may transmit the message in response to a button, such as a housekeeping button, on the bed being pressed by a person.

A network interface unit may be couplable to bed communications circuitry of a hospital bed and may be configured to communicate data via a data link to a hospital Ethernet. The data link may comprise a wired data link, a wireless data link, or both. The network interface unit may be configured to convert data received from the bed in a format according to a first protocol into a format according to a second protocol, such as an Ethernet protocol. The network interface unit may be coupled to a legacy (i.e., existing) nurse call system and data formatted according to the first protocol may be fed through the network interface unit and communicated to the legacy nurse call system while remaining formatted according to the first protocol.

A hospital bed contemplated by this disclosure may comprise bed control circuitry for controlling a plurality functions of the bed and for monitoring at least some of the plurality of functions. The hospital bed may also comprise a network interface circuit that is coupleable to a hospital Ethernet via a data link. The data link may comprise a wired data link, a wireless data link, or both. The network interface circuit may be configured to format data received from the bed control circuitry into a format according to an Ethernet protocol.

A system according to this disclosure may comprise at least one computer device coupled to a hospital Ethernet which may have at least one wired access point and at least on wireless access point. The system may comprise a hospital bed having associated therewith bed identification (ID) data. The system may also comprise a network interface unit (NIU) coupled to the bed via a first data link. The NIU may have associated therewith NIU ID data. The NIU may have a communications port that is coupleable to the Ethernet via a second data link. The NIU may be configured to sense whether the communications port is coupled to the Ethernet via the second data link. If the NIU is coupled to the Ethernet via the second data link then both the bed ID data received by the NIU and the NIU ID data may be transmitted by the NIU to the Ethernet over the second data link. However, if the NIU is not coupled to the Ethernet via the second data link then the NIU ID data received by the bed may be transmitted wirelessly by the bed to one of the wireless access points of the Ethernet along with the bed ID data.

Additional features, which alone or in combination with any other feature(s), such as those listed above, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures, in which.

DETAILED DESCRIPTION OF THE DRAWINGS

Figure 1:
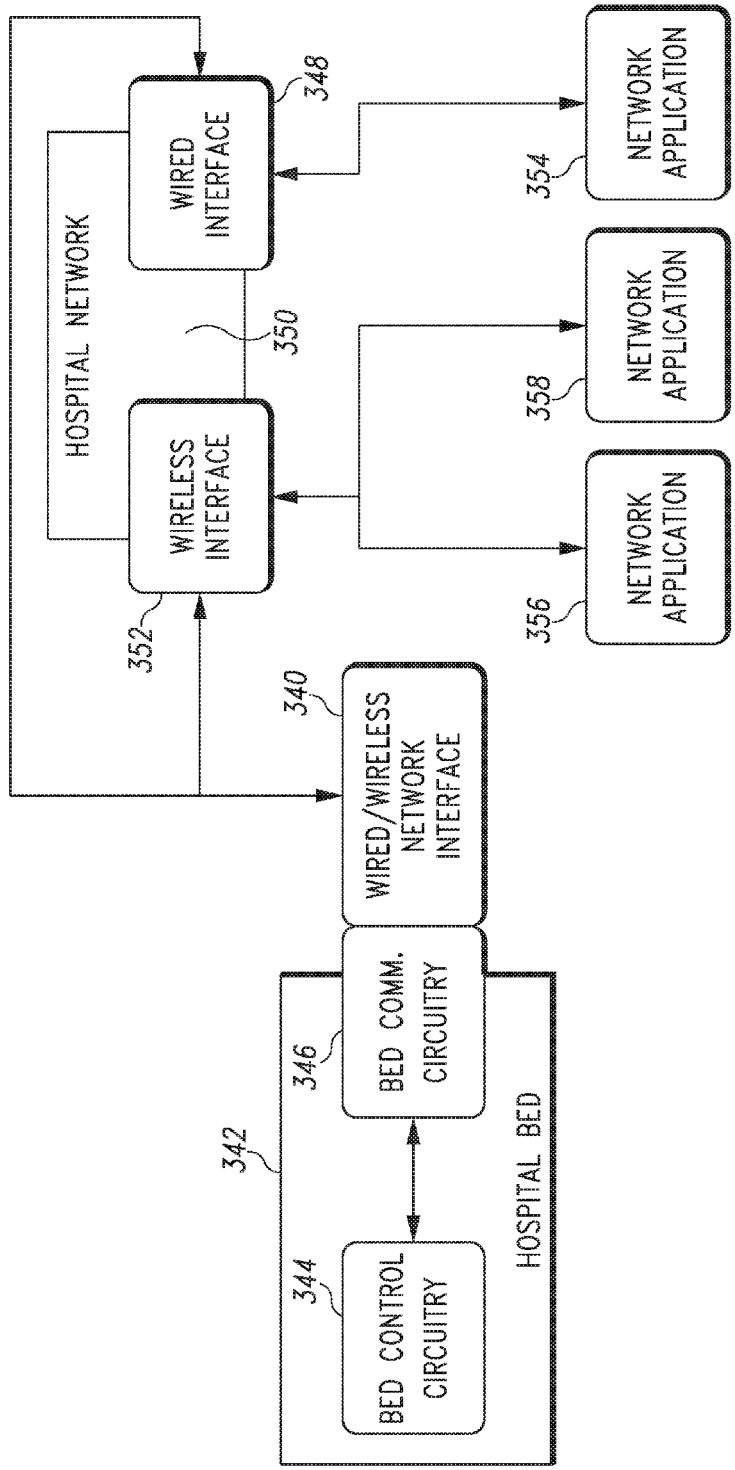
FIG. 1 is a block diagram showing a hospital bed having bed communication circuitry and a wired/wireless network interface unit that is coupled to the bed communication circuitry and that is configured for communication with a hospital network via a wired interface and/or a wireless interface.

According to this disclosure a network interface unit 340 couples to a hospital bed 342 as shown in FIG. 1. Bed 342 includes bed control circuitry 344 which controls the various functions of bed 342 and that monitors the status of various bed functions. Bed 342 also includes bed communication circuitry 346 through which bed status data is communicated. Bed communications circuitry 346 includes a communications port designed for mating with a connector of a nurse call cable, such as a cable having a 37-pin connector, which, in turn, couples to a nurse call system. Interface unit 340 couples to the connector of circuitry 346, such as via a pigtail connector extending from a housing of unit 340, in lieu of the nurse call cable.

Unit 340 includes protocol conversion circuitry that converts the data which is received from bed 342 and which is formatted according to a first protocol, such as a serial peripheral interface protocol (e.g., the interface protocol described in U.S. Pat. No. 6,362,725) into a format according to a second protocol, such as a standard Ethernet protocol including the 802.11b wireless communication protocol. Unit 340 includes a communications port, such as an RJ-45 port, which is couplable via a cable to a wired interface 348 of a hospital network or Ethernet 350. Interface 348 is an RJ-45 port in some embodiments. Unit 340 also includes circuitry for communicating wirelessly with a wireless interface 352 of Ethernet 350. In some embodiments, interface 352 comprises a wireless transceiver, such as an 802.11 access point. Thus, data received from bed 342 by unit 340 according to the first protocol is sent to interface 348 and/or interface 352 according to the second protocol. In addition, data received by unit 340 from network 350 according to the second protocol is converted by unit 340 into the format associated with the first protocol and then forwarded on to circuitry 344 of bed 342 through circuitry 346. In some embodiments, unit 340 is configured to couple only to one or the other of interfaces 348, 352. In some embodiments, the protocol conversion circuitry is omitted from unit 340 such that data is transmitted by unit 340 according to the same protocol in which the data was received from bed 340 and network 350 transmits data to unit 340 according to this same protocol.

In the illustrative example, data communicated from unit 340 to wired interface 348 is provided to a first network application 354 and data communicated from unit 340 to wireless interface 352 is provided to a second network application 356 and to a third network application 358. Network applications include, for example, nurse call system software, admission-discharge-tracking (ADT) system software, electronic medical records (EMR) system software, workflow system software, medical records archiving system software, and the like. Two or more of these software applications are stored in the same computer device, such as a server, in some embodiments. It is contemplated by this disclosure that a first subset of bed data is communicated to interface 348, but not to interface 352, and that a second subset of bed data is communicated to interface 352, but not to interface 348. It is also contemplated by this disclosure that the same bed data is communicated to both interfaces 348, 352.

In some embodiments, unit 340 includes circuitry that determines whether or not unit 340 is coupled to interface 348. In such embodiments, if unit 340 is coupled to interface 348, then bed data will be communicated via the wired data link to interface 348 and no attempts will be made by unit 340 to communicate with interface 352. If, on the other hand, unit 340 is not coupled to interface 348, then bed data will be communicated via the wireless data link to interface 352. Unit 340 may be coupled to interface 348, for example, when bed 342 is stationary in a hospital room and unit 340 may be uncoupled from interface 348, for example, when bed 342 is being transported through a healthcare facility from one location to another. Thus, unit 340 permits wireless communication with network 350 during transport of bed 342.

Figure 2:
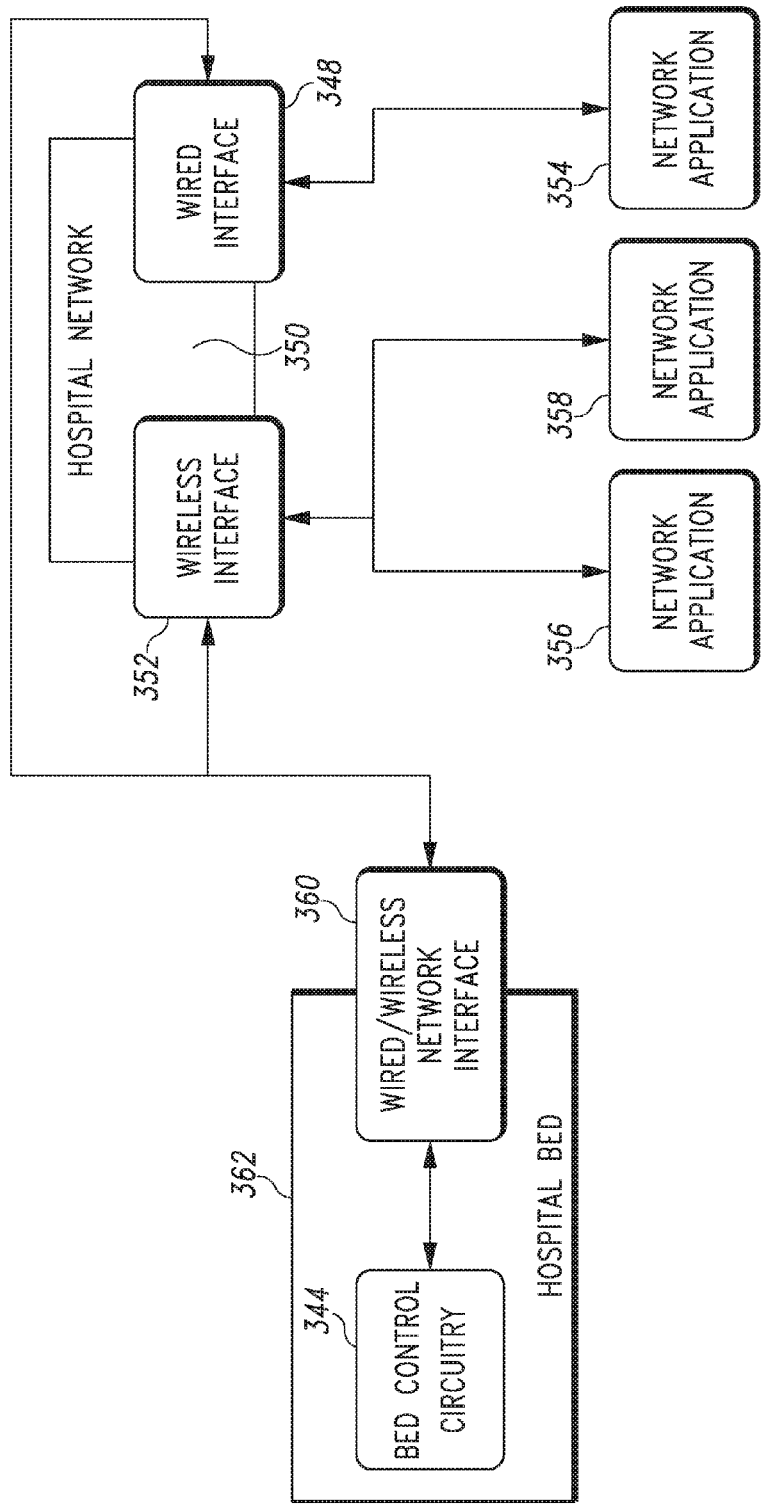
FIG. 2 is a block diagram, similar to FIG. 1, showing a wired/wireless network interface unit integrated into the circuitry of the bed.

Based on the foregoing description, it will be appreciated that units 340 may be used to retrofit existing hospital beds with the ability to communicate with a hospital Ethernet either wirelessly and/or via a wired connection according to an Ethernet protocol. However, hospital beds manufactured with the circuitry and functionality of units 340 included therein are within the scope of this disclosure as depicted in FIG. 2 in which a network interface unit 360 is included as part of a hospital bed 362. Portions of FIG. 2 that are the same as, or substantially similar to, like portions of FIG. 1 are denoted with like reference numerals. In some embodiments, network interface units 340, 360 may include connection ports for nurse call cables to provide feed through of bed data to legacy (i.e., existing) nurse call systems which are not otherwise able to communicate with beds 342, 362 via the hospital Ethernet.

An electric circuit schematic of one embodiment of unit 340 is attached as Appendix 1 to U.S. Provisional Application No. 60/773,286 which already is incorporated by reference herein and which will be accessible via the USPTO website when the present application is published. As mentioned above, in some embodiments, unit 340 communicates only wirelessly such that unit communicates with wireless interface 352 of network 350 but not wired interface 348. In such embodiments, bed communications circuitry 346 may include a connection port for coupling to wired interface 348. Unit 340 is sometimes referred to herein as a "wireless communications module."

According to this disclosure, hospital beds that were designed originally to transmit a limited set of bed status data are retrofitted with circuitry to permit an increased set of bed status data to be transmitted from unit 340 wirelessly and/or via a wired connection. Of course, beds manufactured originally with the capability to transmit the increased set of bed status data are contemplated by this disclosure as well. In such beds to be retrofitted with circuitry to permit an increased set of bed status data to be transmitted, existing circuitry 346 is removed and new bed communications circuitry 346 is installed in its place. In some embodiments of these retrofitted beds, unit 340 is configured to wirelessly transmit the increased set of bed status data wirelessly, whereas the bed circuitry 344 and/or the retrofitted circuitry 346 may be configured to transmit the original set of bed status data via a wired connection to network 350. An electric circuit schematic of one embodiment of circuitry 346 which is designed to be retrofitted and/or to be installed originally on the VersaCare™ bed marketed by Hill-Rom Company, Inc. was attached as Appendix 2 to U.S. Provisional Application No. 60/773,286 which already is incorporated by reference herein and which will be accessible via the USPTO website when the present application is published. An electric circuit schematic of another embodiment of circuitry 346 which is designed to be retrofitted and/or to be installed originally on the TotalCare® bed marketed by Hill-Rom Company, Inc. was attached as Appendix 3 to U.S. Provisional Application No. 60/773,286.

One example of bed status data transmitted wirelessly by unit 340 from bed 342 is given below in Tables 1-3.

TABLE 1

| 0x04 Bed Status Messages | | 0x04 Location Byte | Bit | Name | ID | Read - R Write - W Auto Broadcast - B | Description |
|---|---|---|---|---|---|---|---|
| Standard Bed Status | Standard Template | | | | | | |
| | Brake Status | 1 | 4 | BedStatus | 0x04 | B | 1 = Brake set, 0 = Brake not set |
| | Surface prevent mode | 1 | 2 | BedStatus | 0x04 | B | 0 = Not activated, 1 = Activated |
| | Fall Prevention | | | | | | |
| | Bed Exit Armed | 1 | 1 | BedStatus | 0x04 | B | 0 = Armed, 1 = Not armed |
| | Bed Low Position | 1 | 3 | BedStatus | 0x04 | B | 0 = Bed not down, 1 = Bed down |
| | Head Rail Positions | 1 | 6 | BedStatus | 0x04 | B | 0 = Not down, 1 = Down |
| | Restraints | | | | | | |
| | Head rail positions | 1 | 6 | BedStatus | 0x04 | B | 0 = Not down, 1 = Down |
| | Foot rail positions | 1 | 5 | BedStatus | 0x04 | B | 0 = Not down, 1 = Down |

As shown in Table 1, brake status data indicates whether a brake for one or more of the casters of the hospital bed is set or not set; surface prevent mode data indicates whether a surface of the hospital bed is or is not activated to control air bladder pressures in a manner which attempts to inhibit formation of pressure ulcers (e.g., bed sores); bed exit armed status to indicate whether or not bed exit system which detects whether or not a patient has exited the bed is armed or not armed; bed low position data to indicate whether or not an upper frame which carries a mattress support deck is in its lowest position relative to a base frame of the bed; head rail position data to indicate whether head end siderails are up or down; and foot rail position data to indicate whether foot end siderails are up or down.

TABLE 2

| Enhanced Bed Status | Enhanced Fall Prevention | | | | | | |
|---|---|---|---|---|---|---|---|
| | PPM mode - Move | 3 | 8 | BedStatus | 0x04 | B | 0 = Not selected, 1 = Mode selected |
| | PPM mode - Start egress | 3 | 7 | BedStatus | 0x04 | B | 0 = Not selected, 1 = Mode selected |
| | PPM mode - Patient exit | 3 | 6 | BedStatus | 0x04 | B | 0 = Not selected, 1 = Mode selected |
| | PPM alarming | 3 | 5 | BedStatus | 0x04 | B | 0 = Not selected, 1 = Mode selected |
| | Enhanced Restraints | | | | | | |
| | Right head rail position | 2 | 1 | BedStatus | 0x04 | B | 0 = Not down, 1 = Down |
| | Left head rail position | 2 | 2 | BedStatus | 0x04 | B | 0 = Not down, 1 = Down |
| | Right foot rail position | 2 | 3 | BedStatus | 0x04 | B | 0 = Not down, 1 = Down |
| | Left foot rail position | 2 | 4 | BedStatus | 0x04 | B | 0 = Not down, 1 = Down |
| | Bed Safety | | | | | | |
| | Head Motor Lockout | 2 | 5 | BedStatus | 0x04 | B | 0 = Not locked, 1 = Locked |
| | Knee Motor Lockout | 2 | 6 | BedStatus | 0x04 | B | 0 = Not locked, 1 = Locked |
| | High-Low Motor Lockout | 2 | 8 | BedStatus | 0x04 | B | 0 = Not locked, 1 = Locked |
| | All Motor Lockout | 2 | 7 | BedStatus | 0x04 | B | 0 = Not locked, 1 = Locked |
| | Wound Prevention | | | | | | |
| | Surface turn assist left mode | 3 | 2 | BedStatus | 0x04 | B | 0 = Not active, 1 = Active |
| | Surface turn assist right mode | 3 | 3 | BedStatus | 0x04 | B | 0 = Not active, 1 = Active |
| | Surface max inflate mode | 3 | 4 | BedStatus | 0x04 | B | 0 = Not active, 1 = Active |
| | Heel suspension mode | 5 | 4 | BedStatus | 0x04 | B | 0 = Not active, 1 = Active |
| | Rotation mode | 5 | 3 | BedStatus | 0x04 | B | 0 = Not active, 1 = Active |
| | Optirest mode | 5 | 2 | BedStatus | 0x04 | B | 0 = Not active, 1 = Active |
| | Pulmonary | | | | | | |
| | Percussion | 4 | 5 | BedStatus | 0x04 | B | 0 = Not active, 1 = Active |
| | Vibration | 4 | 6 | BedStatus | 0x04 | B | 0 = Not active, 1 = Active |
| | Operational Alerts | | | | | | |
| | Housekeeping | 5 | 1 | BedStatus | 0x04 | B | 0 = Not active, 1 = Active (switch status, not bed cleaned status) |

TABLE 2-continued

| Maintenance Alerts | | | | | | |
|---|---|---|---|---|---|---|
| Battery status modes, 2 bits | 4 | 2 | BedStatus | 0x04 | B | 0 0 = No battery present |
| | 4 | 3 | BedStatus | 0x04 | B | 0 1 = Battery disconnected |
| | | | | | | 1 0 = Battery needs charging |
| | | | | | | 1 1 = Battery fully charged |
| AC power not present mode | 4 | 1 | BedStatus | 0x04 | B | 1 = AC present, 0 = AC not present |
| Service required light | 4 | 4 | BedStatus | 0x04 | B | 0 = No service req'd, 1 = Service req'd |
| Other Bed Data | | | | | | |
| CPR mode | 3 | 1 | BedStatus | 0x04 | B | 0 = Not active, 1 = Active |
| AC power present mode | 4 | 1 | BedStatus | 0x04 | B | 1 = AC present, 0 = AC not present |
| Nurse Call switch | 4 | 7 | BedStatus | 0x04 | B | 0 = Not active, 1 = Active |
| CareAlert Switch | 4 | 8 | BedStatus | 0x04 | B | 0 = Not active, 1 = Active |

As shown in Table 2, patient position mode data indicates whether or not a patient position monitoring system of the hospital bed is in move mode in which patient movement of a first amount is considered an alarm condition, a start egress mode in which patient movement of a second amount greater than the first amount is considered an alarm condition, or patient exit mode in which patient movement of a third amount greater than the second amount (including movement off of the bed) is considered an alarm condition, and the patient position mode data also indicates whether or not an alarm condition, of the selected mode, has occurred. As also shown in Table 2, siderail position data indicates whether each of a right head rail, a left head rail, a right foot rail, and a left foot rail are in up or down positions; motor lockout data indicates whether or not a head motor which is operable to raise and lower a head section of the mattress support deck is locked out; whether or not a knee motor which is operable to raise and lower a thigh section (or seat section) of the mattress support deck is locked out; whether or not one or more high-low motors which are operable to raise and lower an upper frame carrying the mattress support deck relative to a base frame of the bed is locked out; and whether or not all of the motors just described are locked out.

Table 2 further shows surface status data such as whether or not a left turn assist mode or right turn assist mode to turn the patient, on a one-time basis, in one direction or another is active; whether or not a max inflate mode to inflate air bladders of the mattress to a preprogrammed maximum pressure to harden the surface for patient transfer, patient ingress or egress, or CPR is active; whether or not a heel suspension mode to deflate bladders in a heel region of the patient to attempt to inhibit formation of pressure ulcers on the patient's heels is active; whether or not a rotation mode to cyclically rotate the patient to the left and to the right is active; whether or not an optirest mode to sequentially inflate head zone bladders, seat zone bladders, and foot zone bladders is active; whether or not percussion to pulsate one or more air bladders of the surface is active; and whether or not vibration to vibrate one or more air bladders of the surface is active. In other embodiments, the surface status data may indicate whether or not a low air loss mode in which air is expelled from openings in the mattress to cool the patient and/or to transport moisture away from the patient is active and/or whether or not an alternating pressure mode in which sets of alternating bladders are each inflated and deflated at different times so that different portions of the patient are primarily supported by different bladders sets at different times is active.

As further shown in Table 2, housekeeping data indicates whether or not a housekeeping switch or button on the bed is active (e.g., has been pressed) to request that a staff member clean the hospital bed and/or the associated room; battery status data indicates whether or not a battery is present on the bed, whether or not the battery is disconnected from bed circuitry, whether or not the battery needs to be charged, and whether or not the battery is fully charged; AC power data indicates whether or not AC power is being received by the bed; service data indicates whether or not the bed needs to serviced; CPR mode data indicates whether or not a CPR release handle of the bed, which causes a head section of the mattress support deck to be lowered rapidly so that CPR can be quickly administered to a patient, has been activated; nurse call data indicates whether or not a nurse call switch to request to speak with a caregiver has been activated; and Care Alert data indicates whether or not a Care Alert switch to enable and disable any Care Alerts set up in templates at a remote computer has been activated. activated.

TABLE 3

| Object Dictionary Data | | | | | | Description |
|---|---|---|---|---|---|---|
| Other | Bed Management | | | | | |
| | Bed Type | 0x02 record | BedType | 0x02 | B | Bed type byte, revision number |
| | Bed Location Pulmonary | 0x05 record | BedLocation | 0x05 | R | Wall ID, 4 bytes |
| | Head Angle | OD entry 0x3262, 0x00 | Pulmonary | <3262000 | R | Object dictionary entry 16-bit unsigned (VC), 16-bit signed (TC) |

TABLE 3-continued

| Object Dictionary Data | | | | | Description |
|---|---|---|---|---|---|
| Switches | | | | | |
| Installed Switches | OD entry 0x3642, 0x00 | ISwitches | <3642000 | R/W | Object dictionary entry |
| | 1 | 4 | | | 1 = brake switch installed 0 = not installed |
| | 1 | 5 | | | 1 = siderail foot switches installed, 0 = not installed |
| | 1 | 6 | | | 1 = siderail head switches installed, 0 = not installed |
| | 1 | 7 | | | 1 = Nurse call switch input available, 0 = not available |
| | 1 | 1 | | | 1 = Bed exit info available, 0 = not available |
| | 1 | 3 | | | 1 = Bed down info available, 0 = not available |
| Weight | | | | | |
| Patient Weight | OD entry | Weight | <2180000 | R | Data in Hex format. Convert to decimal divide by 10 to get weight in pounds. |

As shown in Table 3, bed type data indicates the type of bed (e.g., manufacturer and model number) transmitting the data; bed location data indicates the location in the healthcare facility at which the bed is located; head angle data indicates an angle at which the head section of the mattress support deck is elevated relative to another portion of the bed, such as an upper frame or another deck section, or relative to horizontal or vertical; switch installed data indicates whether or not one or more brake switches, siderail foot switches, siderail head switches, and/or nurse call switches are installed on the bed; information availability data to indicate whether or not bed exit data and/or bed low position data is available from the bed; and patient weight data indicates the weight of a patient as measured by a weigh scale system of the hospital bed.

Table 1 above includes a list of standard bed status data similar to that shown and described in U.S. Pat. Nos. 5,561,412 and 5,699,038. However, according to this disclosure, the standard bed status data is transmitted wirelessly by unit 340 or unit 360 to wireless interface 352. Tables 2 and 3 above each include a list of additional data transmitted wirelessly from unit 340 or unit 360 to wireless interface 352. Additionally or alternatively, any of the bed status data in any of the three above tables may be transmitted from bed 342 or bed 362 to wired interface 348. The data is then used by one or more network applications 354, 356, 358 such as nurse call software which operates to contact assigned caregivers when certain conditions on the bed are detected, workflow software to assign tasks to caregivers and other staff members, locating-and-tracking software to track the whereabouts of people and/or equipment, admission discharge and transfer (ADT) software, bed assignment software, and the like.

Figure 3:
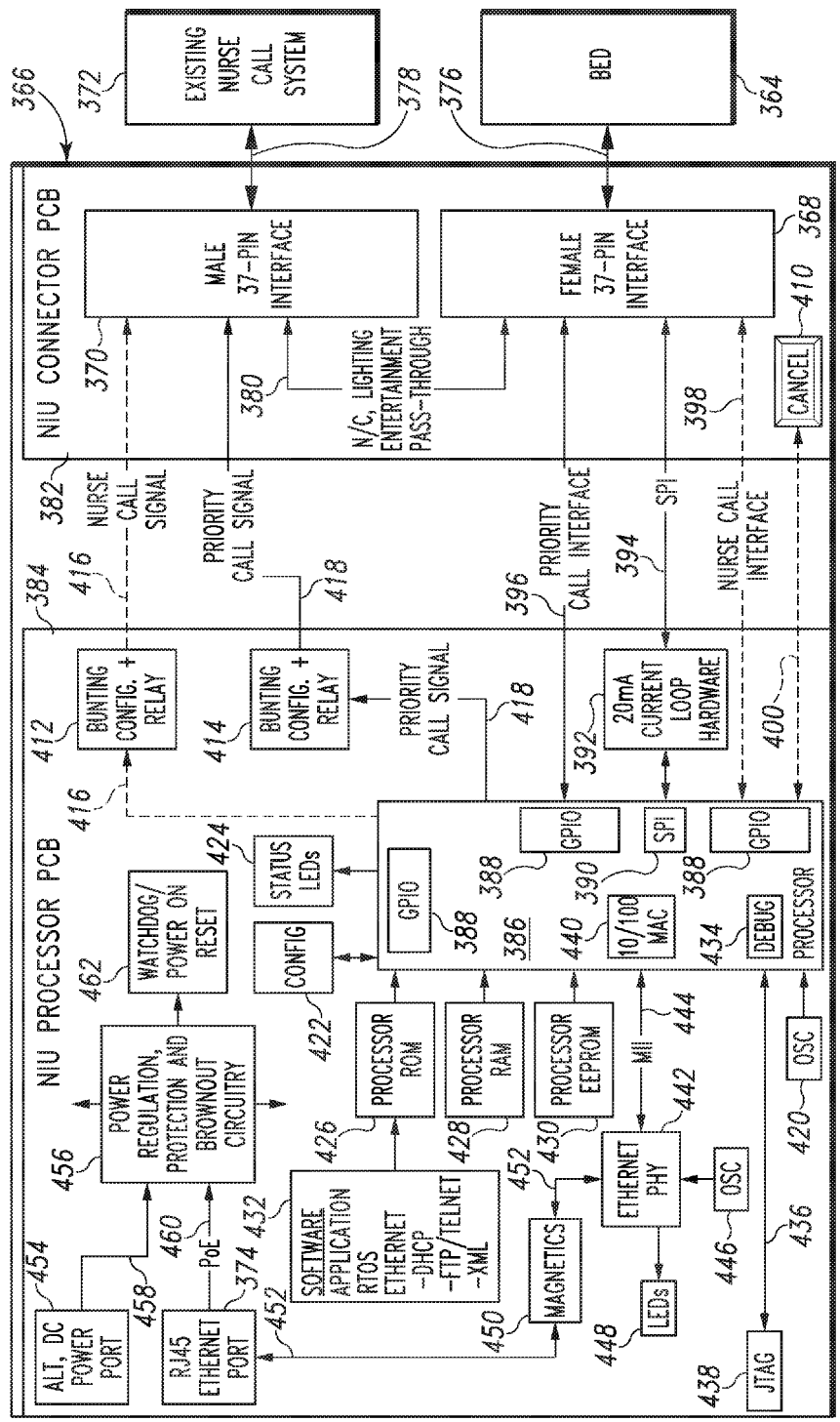
FIG. 3 is a block diagram of a network interface unit which has couplers for coupling to a bed, a nurse call system, and a hospital Ethernet.

A network interface unit 366 which is used with a bed 364, but which is not mounted to or integrated into the bed like units 340, 360 discussed above, includes a first coupler or connector 368 which is coupleable to bed 364, a second coupler or connector 370 which is coupleable to a nurse call system 372, and a third coupler or connector 374 which is coupleable to a hospital Ethernet as shown in FIG. 3. Unit 366 may be mounted, for example, to a room wall or to a head wall unit in a hospital room. In the illustrative example, coupler 368 comprises a female 37-pin interface that mates with a male 37-pin connector provided at the end of a cable extending from bed 364. Also in the illustrative example, coupler 370 comprises a male 37-pin interface that mates with a female 37-pin connector provided at the end of a cable that couples to nurse call system 372. Illustrative connector 374 comprises an RJ-45 Ethernet port which allows unit 366 to be coupled to the hospital Ethernet via an appropriate cable. Thus, connector 374 is sometimes referred to herein as "port 374."

When bed 364 is coupled to connector 368 and nurse call system 372 is coupled to connector 370, communications between bed 364 and nurse call system 372 take place over a first data link 376, a second data link 378, and a feed through data link 380. Data link 376 is established between bed 364 and connector 368. Data link 378 is established between connector 370 and nurse call system 372. Data link 380 is established between connector 368 and connector 370. While data links 376, 378, 380 are typically wired data links, it is within in the scope of this disclosure for one or more of data links 376, 378, 380 to be wireless data links, such as infrared (IR) or radio frequency (RF) data links. In the illustrative example, connectors 368, 370 are mounted to a connector printed circuit board (PCB) 382.

As mentioned above, connector 374 permits unit 366 to be coupled to a hospital Ethernet. Thus, data received from bed 364 and nurse call system 372 via data links 376, 378 may be transmitted to other devices included in the hospital Ethernet through port 374. Port 374 is coupled to a processor PCB 384 to which is also coupled a processor 386 which operates under software control to convert data received from bed 364 and system 372 from the received format into an appropriate format according to an Ethernet protocol, such as the TCP/IP protocol. Processor 386 has a set of general purpose input/output (GPIO) connectors 388 and a serial peripheral interface (SPI) connector 390. Connector 390 is coupled to 20 milliamp (mA) current loop hardware 392 which, in turn, is coupled to connector 368 for communication of a SPI signal 394. Connector 368 is also coupled to connectors 388 of processor 386 for communication of a priority call interface signal 396, a nurse call interface signal 398, and a nurse call cancel signal 400 which is received from a cancel button 410 that is coupled to PCB 382.

Connector 370 is coupled to connectors 388 of processor 386 through a first relay 412 and a second relay 414 for communication of a nurse call signal 416 and a priority call signal 418, respectively. Processor 386 is also coupled to an oscillator 420, a configuration module 422, and a set of status light emitting diodes (LED's) 424. Various memory devices, such as read only memory (ROM) 426, random access memory (RAM) 428, and an Electrically Erasable Programmable Read Only Memory (EEPROM) 430 are also coupled to processor 386. Various software applications 432 are stored in the memory devices for execution by processor 386. In the illustrative example, software applications 432 are stored in ROM 426 and include real time operating system (RTOS) software and Ethernet software such as Dynamic Host Configuration Protocol (DHCP) software, file transfer protocol (FTP)/telnet software, and extensible markup language (XML) software. The given software types are intended to be exemplary, not exhaustive. Therefore, it is within the scope of this disclosure for all types of software allowing communications between unit 466 and a hospital Ethernet to be stored in one or more of devices 426, 428, 430 and executed by processor 386.

Illustratively, processor 386 includes a debug module 434 which is coupled via a data link 436 to a Joint Test Action Group (JTAG) connector 438. A diagnostic device may couple to connector 438 and perform boundary scanning to read and set the value of the pins of processor 386 and optionally, to read and set the value of other devices on PCB 384 and/or the internal registers of processor 386. Illustrative processor further includes a 10/100 media access controller (MAC) module 440 which operates to permit unit 366 to communicate with the hospital Ethernet at a data transmission rate of 10 Megabits per second (Mbps) or 100 Mbps. Module 440 is coupled to an Ethernet physical layer (PHY) module 442 for communication of Media Independent Interface (MII) signals 444. Module 442 is coupled to an oscillator 446 and a set of LED's 448. Module 442 is also coupled to, or optionally includes, an electrical isolation device 450 such as a transformer. Device 450 electrically isolates the data signals communicated on a data link 452 between module 442 and connector 374.

Unit 466 includes an alternative direct current (DC) power port 454 which is coupled to power regulation, protection, and brownout circuitry 456 by one or more power conductors 458. Power from an external source is coupleable to port 454 and is used for operating the various components of unit 366. One or more power over Ethernet (PoE) conductors 460 are also coupled to circuitry 456 so that, if connector 374 is coupled to the hospital Ethernet, power from the Ethernet may be used for operating the components of unit 366. Circuitry 456 is also coupled to a Watchdog/Power On Reset circuit 462. Additional details of one embodiment of unit 366 in accordance with this disclosure, including an electric circuit schematic thereof, are shown in Appendix 4 which is attached hereto and considered to be part of this provisional patent application.

As mentioned above, unit 366 is coupleable via connectors 368, 370, 374 to bed 364, nurse call system 372, and the hospital Ethernet, respectively. In the illustrative example, nurse call system 372 does not communicate according to an Ethernet protocol, but rather unit 366 provides a connection between nurse call system 372 and the Ethernet and converts data from system 372 into the appropriate format for Ethernet communication. In alternative arrangements, nurse call system 372 is not coupled to connector 370 via data link 378, but rather nurse call system 372 is configured to communicate via an Ethernet protocol and sends data to, and receives data from, unit 366 via port 374. In such alternative arrangements, unit 366 converts the data received via port 374 from the nurse call system into the appropriate format for communication to bed 364 via connector 368 and data link 376.

Figure 4:
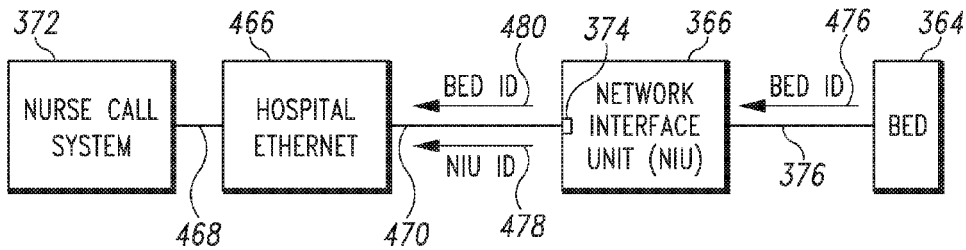
FIG. 4 is a block diagram showing a hospital bed coupled to a nurse call system through the network interface unit and the hospital Ethernet.
Figure 5:
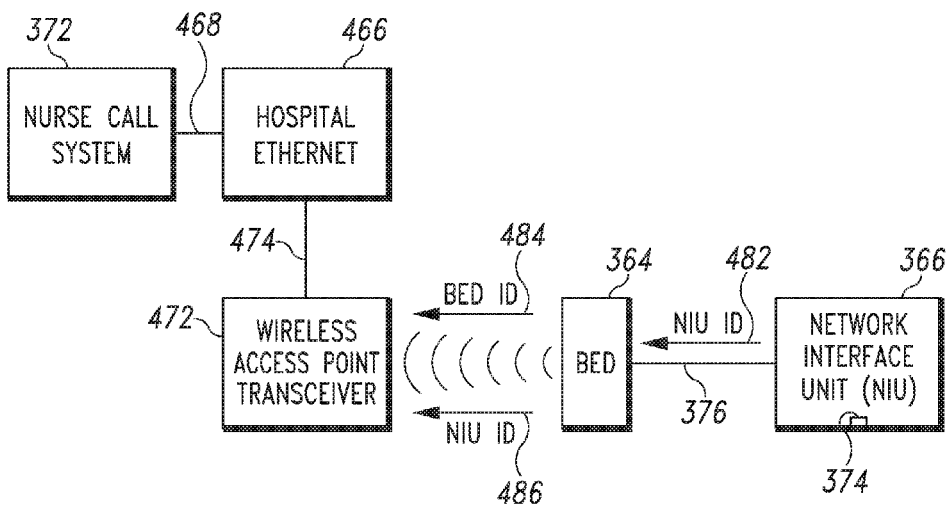
FIG. 5 is a block diagram showing a hospital bed coupled to the network interface unit and communicating wirelessly with the hospital Ethernet.

Referring now to FIG. 4, nurse call system 372 is coupled to a hospital Ethernet 466 via a data link 468 and bed 364 is coupled to network interface unit (NIU) 366 via data link 376. Unit 366 is, in turn, coupled to Ethernet 466 via a data link 470 which is coupled to port 374 of unit 366. Data links 376, 468, 470 are typically wired data links. However, it is within the scope of this disclosure for data links 376, 468, 470 to be wireless. Referring now to FIG. 5, an alternative arrangement is shown in which bed 364 is configured to communicate wirelessly with a wireless access point transceiver 472 that is coupled to Ethernet 466. Bed 364 communicates bidirectionally with transceiver 472 according to an appropriate Ethernet protocol and transceiver 472 communicates bidirectionally with Ethernet 466 via a data link 474.

It will be appreciated that a hospital will have multiple beds, similar to bed 364, and multiple network interface units 366 associated with the various beds. Each unit 366 is mounted at a particular location in a hospital. For example, one or more units 366 will be located in various patient rooms. Each bed 364 and each unit 366 is assigned a unique identification (ID) code, such as a serial number. In some embodiments, one or more of the computer devices of nurse call system 372 have software that operates to associate bed ID data with NIU ID data so that system 372 can keep track of which bed is located in each room of the hospital and convey this information to caregivers using system 372.

Processor 386 of unit 366 operates to determine whether or not port 374 is coupled to Ethernet 466. Depending upon whether or not the unit 366 is connected to Ethernet 466 via port 374, the data path of the bed ID data and the NIU ID data to nurse call system 372 is different. If unit 366 senses that port 374 is coupled to Ethernet 466 as shown in FIG. 4, for example, then the associated bed 364 sends its bed ID data to the unit 366, as indicated by arrow 476, and then unit 366 communicates its NIU ID data and the bed's ID data to Ethernet 466 in packets through port 374 as indicated by arrows 478, 480, respectively. If unit 366 senses that port 374 is not coupled to Ethernet 466, as shown in FIG. 5, for example, then unit 366 sends its NIU ID data to the associated bed 364, as indicated by arrow 482, and then bed 364 wirelessly transmits its bed ID data and the NIU ID data to transceiver 472 in wireless packets as indicated by arrows 484, 486, respectively. The data path for other types of bed status data is the same path as that for bed ID data shown in FIGS. 4 and 5 depending upon whether or not unit 366 is connected to Ethernet via port 374.

Beds 342, 362, 364 each have power cords (not shown) that are plugged into electrical outlets in hospital rooms during normal use of the beds 342, 362, 364, regardless of whether the beds 342, 362, 364 communicate with other devices in the associated network via wired or wireless connections. According to this disclosure, when the power cords of beds 342, 362, 364 are unplugged, which usually happens when the bed is to be moved from one location in a healthcare facility to another, the associated Care Alert templates, such as those discussed below in connection with FIGS. 10 and 11 and/or those discussed in U.S. patent application Ser. No. 11/189,781 which is incorporated by reference herein, are automatically disabled. Thus, even if the bed 342, 362, 364 is still able to communicate bed data wirelessly during transit from one location to another, the associated nurse call system does not initiate any communications with the wireless communication devices carried by the caregivers. Such alarm notifications are not generally needed because other caregivers should be accompanying the bed 342, 362, 364 during transit. Before the automatic disabling of the Care Alert templates, a slight delay period, such as 10 or 20 seconds, may be required to elapse so that, if the bed's power plug was unplugged inadvertently, there is time to plug the bed back in before the Care Alert templates are disabled.

In the case of beds 342, 362, 364 that communicate wirelessly, data is sent from the bed's wireless transmitter to notify the associated nurse call system that the bed has been unplugged. Such data may be transmitted after the above-mentioned delay period (i.e., the bed determines when the delay period has elapsed) or substantially immediately in response to the bed being unplugged (i.e., the nurse call system determines when the delay period has elapsed). In the latter case, appropriate data is sent from the bed's wireless transmitter if the bed is plugged back in before the delay period elapses so that the nurse call system does not disable the Care Alert template.

Beds having wireless communication circuitry may be powered by battery back-up power or by one or more capacitors for a period of time sufficient to permit the transmission of data indicating that the bed has been unplugged (and, in some embodiments, for a return acknowledgment to be received by the bed). In the case of beds 342, 362, 364 coupled to NIU 366, the NIU 366 sends appropriate signals to the nurse call system indicating either that the power cord of the bed has been unplugged or that the bed has been unplugged from the NIU 366. Additionally or alternatively, the nurse call system may also conclude that the bed 342, 362, 364 has been unplugged and is in transit if a different wireless transceiver or receiver receives a signal from the bed 342, 362, 364, such as a wireless access point or a transceiver of an associated locating-and-tracking system, and proceed to automatically disable the Care Alert alarm notifications as a result.

In some embodiments, after the bed 342, 362, 364 reaches its new location and the associated power cord is plugged back in, a caregiver signals the nurse call system to re-enable the Care Alert templates for the particular bed. Caregivers may re-enable the Care Alert templates for the particular bed 342, 362, 364 by making appropriate entries on either an audio station in the room, a computer at the master nurse call station, or the wireless communication device carried by the caregiver. The re-enabling of the Care Alert template may be made by voice commands entered into the wireless communication device in some embodiments.

Because the nurse call system receives bed ID data, the particular Care Alert template associated with the bed 342, 362, 364 is known by the nurse call system. Thus, unless overridden by users of the nurse call system, the association between bed, patient, and assigned caregivers is maintained by the nurse call system even if the bed is moved to a new location. If one of the assigned caregivers does not re-enable the Care Alert template within a predetermined period of time after the nurse call system determines that the bed has been plugged back in (such determination being made in any of the ways described above for determining that the bed has been unplugged), then a reminder to re-enable the Care Alert template may be initiated by the nurse call system to the wireless communication devices carried by one or more of the assigned caregivers.

In alternative embodiments, the nurse call system may re-enable the Care Alert templates automatically after bed 342, 362, 364 has been moved and then plugged back in. Alternatively or additionally, the nurse call system may initiate a communication to the wireless communication devices of one or more assigned caregivers advising that the nurse call system will re-enable the Care Alert templates within a predetermined period of time unless receiving instructions not to do so. Alternatively or additionally, the nurse call system may initiate a communication to the wireless communication devices of one or more assigned caregivers with a notification that an assigned bed is now determined to be at a new location and the one or more caregivers should communicate via appropriate measures (entries on a nurse call computer, voice commands, entries on a user interface of a wireless communication device, etc.) to re-enable the associated Care Alert templates.

The data received from beds 342, 362, 364 by the associated nurse call system may be provided to other systems of the hospital network. In one example, beds 342, 362, 364 having weigh scale systems transmit patient weight to a nurse call system which, in turn, transmits the patient weight data to an electronic medical records (EMR) system which, in turn, stores the weight information in the associated patient's record. The nurse call system may convert the data from one communication protocol into another communication protocol. Thus, patient weight data received by the nurse call system may be converted by the system into the Health Level 7 (HL7) protocol for transmission to the EMR system. In some embodiments, patient weight data is transmitted to the nurse call system only in response to a query initiated by a caregiver via entries on a nurse call computer, voice commands, entries on a user interface of a wireless communication device, etc. Such a system reduces extraneous data transmissions on the network for data, such as patient weight, of the type which does not vary much with time and which may be desired by caregivers only sporadically.

Hospital computer networks are usually coupled to the Internet. Accordingly, because beds 342, 362, 364 are coupled to the hospital network, data from beds 342, 362, 364 may be made available on the Internet. Such data is password protected in some embodiments. In addition, software upgrades may be communicated to beds 342, 362, 364 and to the nurse call system by the bed manufacturer and the nurse call system manufacturer, for example, over the Internet and/or hospital network. The software upgrades to the bed may be received from the hospital network wirelessly or via a wired connection to the hospital network. Additionally or alternatively, the software of the nurse call system and/or bed may be field upgradeable via a computer that a field technician couples to the hospital network while visiting the facility.

Different types of hospital beds have different features and functions. Thus, beds 342, 362, 364 may not have all of the types of functions that may be configured on certain ones of the Care Alert templates. For example, not all beds have bed exit systems or weigh scale systems. As another example, many beds don't have specialized therapy surfaces such as rotation surfaces, low-air-loss surfaces, or alternating pressure surfaces. According to this disclosure, beds 342, 362, 364 transmit data to the associated nurse call system which indicates the bed configuration (e.g., the types of functions with which the bed is equipped). In some embodiments, the nurse call system "grays out" (e.g., renders unusable) the portions of any Care Alert templates corresponding to feature and functions not present on the associated bed. In other embodiments, the nurse call system removes such features or functions from the Care Alert templates altogether. In still other embodiments, the nurse call system may provide a notification at the master nurse call station and/or via a transmission to an assigned caregiver's wireless communication device to indicate that a particular bed lacks a particular function included on a particular Care Alert template that the user is attempting to configure for the particular bed. Such notifications may also be provided by the nurse call system in those situations where a Care Alert template is first assigned to a patient (such as via the ADT system as described above) and then, subsequently, a bed lacking certain features or functions is assigned to the patient.

Figure 6:
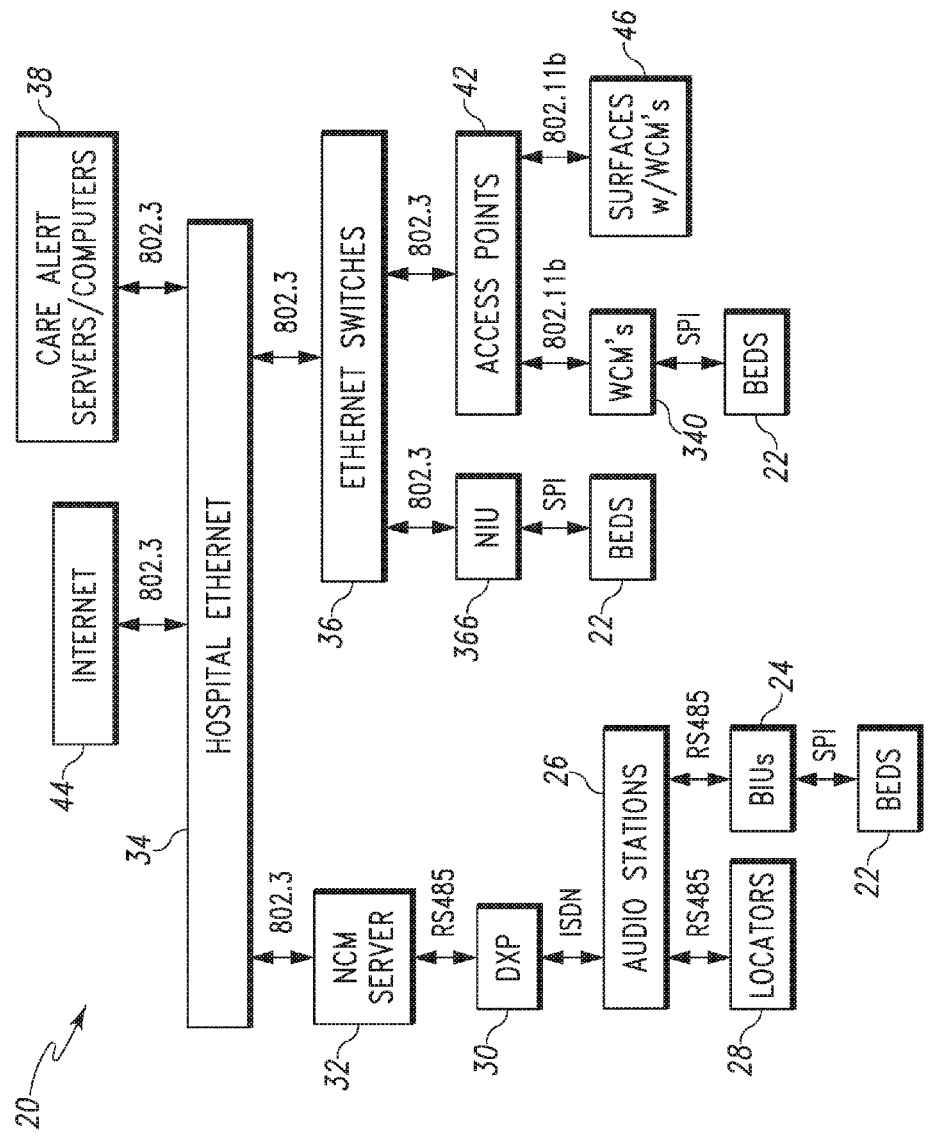
FIG. 6 is a block diagram showing multiple communication paths from hospital beds, surfaces, and locators to a hospital Ethernet, the Internet, and one or more nurse call servers and/or computers.

Referring now to FIG. 6, a network 20 includes a plurality of beds 22 which are configured to communicate with other devices of network 20 in three different ways. For example, beds 22 are couplable to bed interface units 24 (BIU's) via a wired serial peripheral interface (SPI) link, such as a 37-pin to 37-pin cable, and the BIU's are coupled to audio stations 26 via a wired RS485 link. Locators 28 (e.g., IR receivers or transceivers) of a locating-and-tracking system are also coupled to audio stations 26 via an RS485 link and are configured to receive wireless signals, such a IR signals, from locating-and-tracking badges that are worn by, or carried by, caregivers. Audio stations 26 are coupled to a Digital Phone Switch (DXP) 30. In other embodiments a Private Branch Exchange (PBX) is used in lieu of DXP 30. DXP 30 is coupled to a nurse call server 32 via an RS485 link. One or more nurse call computers are coupled to server 32 and display bed status information and other information received by server 32 from beds 22 through BIU's 24, audio stations 26, and one or more DXP's 30. Server 32 and the associated one or more computers are sometimes referred to as a nurse call module (NCM). Server 32 is sometimes referred to herein simply as computer 32. In essence, beds 22, BIU's 24, audio stations 26, locators 28, DXP 30, and server 32 comprises a "legacy" nurse call system of network 20. Such a legacy nurse call system is of the type shown and described in U.S. Pat. Nos. 5,561,412 and 5,699,038. When coupled to a legacy nurse call system in this manner, beds 22 transmit to server 32 "standard bed status data" of the type listed above in this disclosure in the first of the three tables. Optionally, server 32 is coupled to a Hospital Ethernet 34 via a wired link, such as one according to the 802.3 protocol which uses a Carrier Sense Multiple Access with Collision Detection (CSMA/CD) Access Method and Physical Layer Specifications-Media Access Control (MAC) Parameters (sometimes referred to herein as an "802.3 link"). Ethernet 34 in FIG. 6 is intended to diagrammatically represent additional computer devices (e.g., PC's, servers, medical equipment, etc.) and additional infrastructure (e.g. cables, outlets, connectors, routers, gateways, etc.) of network 20.

Beds 22 are also couplable to network interface units (NIU's) 366 via a wired SPI link. NIU's 366 of network 20 are substantially the same as NIU 366 described above in connection with FIGS. 3-5 and so the same reference numeral is used for NIU's 366 in FIG. 6. NIU's 366 are coupled to Ethernet switches 36 via 802.3 links and switches 36 are coupled to Hospital Ethernet 34 via 802.3 links. One or more Care Alert servers and/or computers 38 (sometimes simply referred to as "computer 38" hereinafter) are coupled to Hospital Ethernet 34, as are other healthcare system such as an ADT system, for example. Care Alert servers and/or computers 38 have one or more software applications that receive bed status data from beds 22. For example, a workflow software application is operable to assign tasks to caregivers and other staff members of a healthcare facility. Such workflow software may be, for example, NaviCare® software available from Hill-Rom Company, Inc. According to this disclosure, the workflow software application of computer 38 assigns tasks to staff members based on information received from beds 22 as will be described in further detail below. Computer 38 may also have a nurse call software application. When beds 22 are coupled to computer 38 through NIU's 366 and the associated network infrastructure (e.g., Ethernet switches 36, Ethernet 34, etc.) then beds 22 transmit to computer 38 an enhanced set of bed status data of the type listed above in Tables 1-3, or a portion thereof depending upon the particular features included on a particular bed 22.

Beds 22 are also capable of communicating wirelessly via wireless communication modules (WCM's) that are included in or attached to beds 22. WCM's are substantially similar to units 340 and/or units 360 discussed above and are denoted as WCM's 340 in FIG. 6. WCM's 340 communicate via a SPI link with the circuitry of the associated beds 22 and communicate via a wireless 802.11b link with wireless access points 42 that are located throughout the healthcare facility and that are coupled to Ethernet switches 36 via 802.3 links. It is within the scope of this disclosure for WCM's to communicate with access points 42 according to any wireless communication protocol, such as an 802.11g protocol, Bluetooth protocol, Zigbee protocol, and so on. As mentioned above, Ethernet switches 36 are coupled to Ethernet 34 which is, in turn, coupled to computer 38 via a 802.3 link. Additionally, Ethernet 34 is coupled to the Internet 44 via an 802.3 link. When beds 22 are coupled to computer 38 through WCM's and the associated network infrastructure, then beds 22 wirelessly transmit to computer 38 an enhanced set of bed status data of the type listed above in the all three tables, or a portion thereof depending upon the particular features included on a particular bed 22.

As is evident from FIG. 6, beds 22 may be coupled to components of a legacy nurse call system, coupled to a nurse call system via wired connections to NIU's 366, or coupled to a nurse call system via wireless connections between WCM's 340 and wireless access points 42. The type of connection made by bed 22 (wired connection to BIU's 23, wired connection to NIU's 366, or wireless connection from WCM's to access points 42) determines the type of bed status data that is transmitted by beds 22. Thus, beds 22 have a plurality of connectivity options according to this disclosure. However it is within the scope of this disclosure for beds 22 to only communicate wirelessly using WCM's or for beds to communicate only by wired connections to NIU's. Computer 38 and computer 32 may be configured to send bed status data to any other computer device coupled to Ethernet 34 and/or Internet 44.

Bed status data from beds 22 may be routed to different computers or to different software applications on the same computer. For example, some bed status data packets may be sent by beds 22 and used by a nurse call software application and other bed status data packets may be sent by beds 22 and used by some other software application, such as a workflow software application. Each of the data packets of bed status data may include a destination address, such an Internet Protocol (IP) address, of the computer for which the particular bed status data is destined. As previously mentioned different bed status data may be destined for different software applications run on the same computer, in which case the IP address included in each packet of bed status data may or may not have the same IP address depending upon whether or not the software applications on the same computer have been assigned different IP addresses. Alternatively or additionally, the bed status data may be routed to different software application, be they on the same computer or different computers, based on the data type. In addition, each of the data packets of bed status data include bed identification data, such as a serial number of the associated bed 22 and/or an IP address and/or a MAC address of the associated bed 22. Furthermore, if known, then each of the data packets of bed status data include location data, such as a room number or other location ID indicating the location of the associated bed 22 in the healthcare facility. In accordance with this disclosure, the IP address of each of beds 22 may be assigned by one or more computer devices included in the Ethernet 34 in accordance with the Dynamic Host Configuration Protocol (DHCP).

Also according to this disclosure, surfaces (e.g., therapy mattresses, air mattresses, specialty mattresses) 46 may also have WCM's, such as units 340, associated therewith. Such surfaces 46 with WCM's are simply referred to herein as "surfaces 46." Surfaces 46 having a control unit in a housing that attaches to a footboard of a bed, or to some other portion of the bed, are generally known in the art. Such surface control units typically have pumps, compressors, blowers, valves, manifolds, and the like, as well as electrical control circuitry and user interfaces to provide control signals to the various other components housed in the control unit. Other surfaces 46 may integrate such a control unit into a foot section of the surface. According to this disclosure, wireless communication circuitry is included in or attached to such a surface control unit and is operable to wirelessly transmit surface status data. The wireless communication circuitry included in a surface 46 is also able to receive wireless messages. Thus, as shown in FIG. 6, surfaces 46 communicate wirelessly with access points 42 via wireless 802.11b links. The discussion above concerning the handling of bed status data packets is equally applicable to surface status data packets. It is contemplated by this disclosure, that a surface (with or without a WCM) may connect to bed 22 via a wired connection and the bed 22 may then wirelessly transmit the surface status data along with the bed status data from its WCM 340. In such embodiments, surface control messages may be received by bed 22 from computer 38 and then communicated to the surface via the wired connection.

Figure 7:
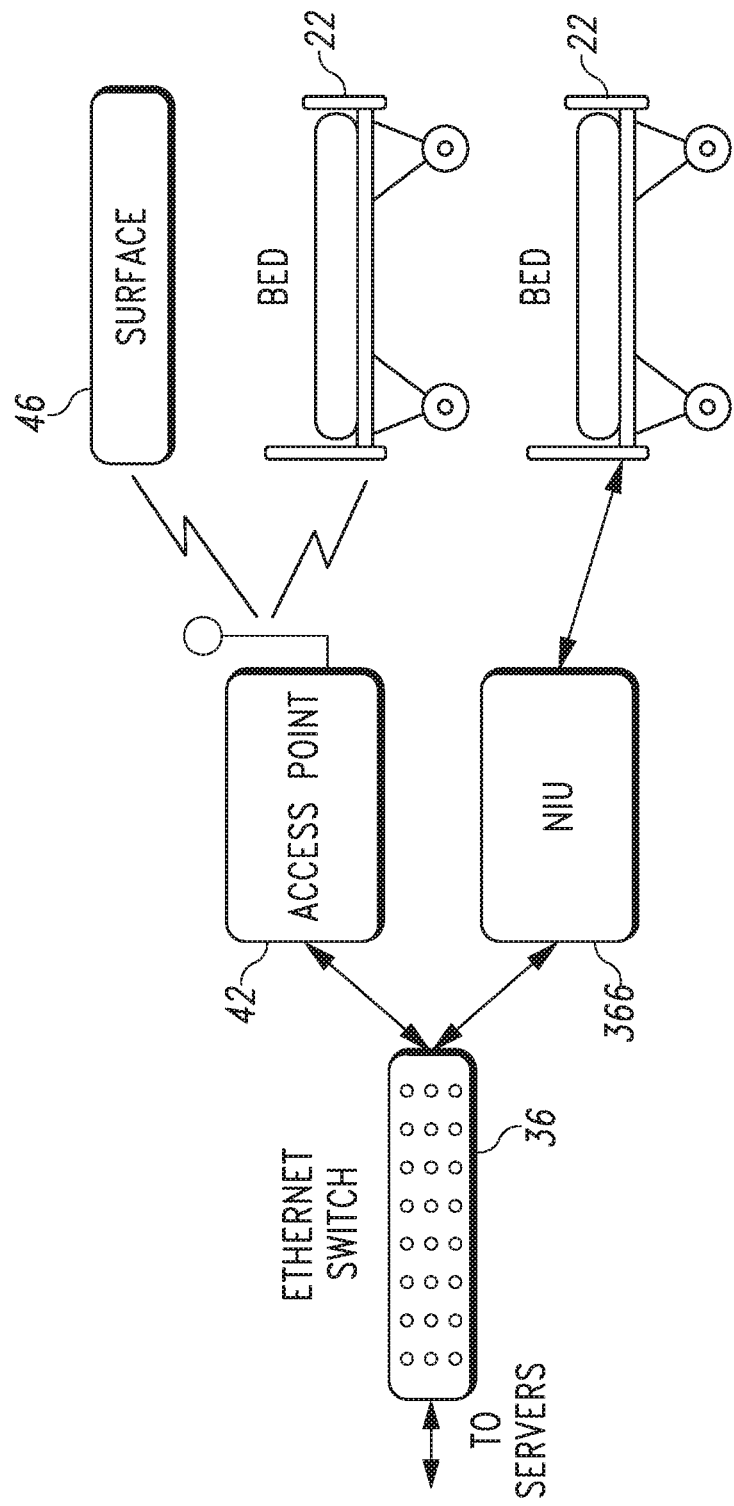
FIG. 7 is a block diagram showing a hospital bed and a surface communicating wirelessly with the same wireless access point, showing a bed communicating with a network interface unit, and showing the wireless access point and the network interface unit communicating with the same Ethernet switch.

As shown diagrammatically in FIG. 7, it is contemplated by this disclosure that a surface 46 having wireless communication capability may be supported on an associated bed 22 which also has wireless communication capability. In such instances, surface 46 and bed 22 may communicate with one or more of the same wireless access points 42 as shown diagrammatically in FIG. 7. Typically, such wireless communication will be at different frequencies and/or at different times, although this need not be the case. Thus, the wireless communication circuitry of bed 22 and the wireless communication circuitry of surface 46 operate independently of each other such that bed 22 transmits its bed status data to computer 38 through the associated network infrastructure and surface 46 transmits its surface status data to computer 38 through the associated network infrastructure.

Computer 38 is operable to send command or control messages through the network infrastructure to beds 22 and surfaces 46 to control some aspect of the operation of beds 22 and surfaces 46. The words "command" and "control" are intended to be interchangeable according to this disclosure and each is intended to have the broad meaning of both. Therefore, computer 38 is operable to receive bed status data from bed 22, process it, and then, based on the bed status data from bed 22, transmit a control message to surface 46. For example, if the bed status data from bed 22 indicates that a CPR release handle of the bed has been pulled, then the control message to surface 46 may result in the surface going into a max inflate mode to harden the air bladders in surface 46 in preparation for CPR being performed on the patient or, alternatively, the control message may result in surface 46 completely deflating so that the patient is supported on underlying bed sections in preparation for CPR being performed on the patient.

As another example, if the bed status data from bed 22 indicates that casters of the hospital bed have been unbraked, then the command message to surface 46 may indicate that a therapy, such as lateral rotation therapy, alternating pressure therapy, percussion therapy, etc. should be stopped in preparation for the bed 22 being moved to a new location. Computer 38 is also operable to receive the surface status data from surface 46, process it, and then, based on the surface status data, transmit a control message to bed 22. For example, if the surface status data indicates that lateral rotation therapy is active, then the control message to bed 22 may lock out a head section motor to prevent the head section of the bed 22 from being raised during the lateral rotation therapy. Computer 38 may be configured to send surface status data to any other computer device coupled to Ethernet 34 and/or Internet 44, including sending surface status data to Workflow Computer System 40.

Figure 8:
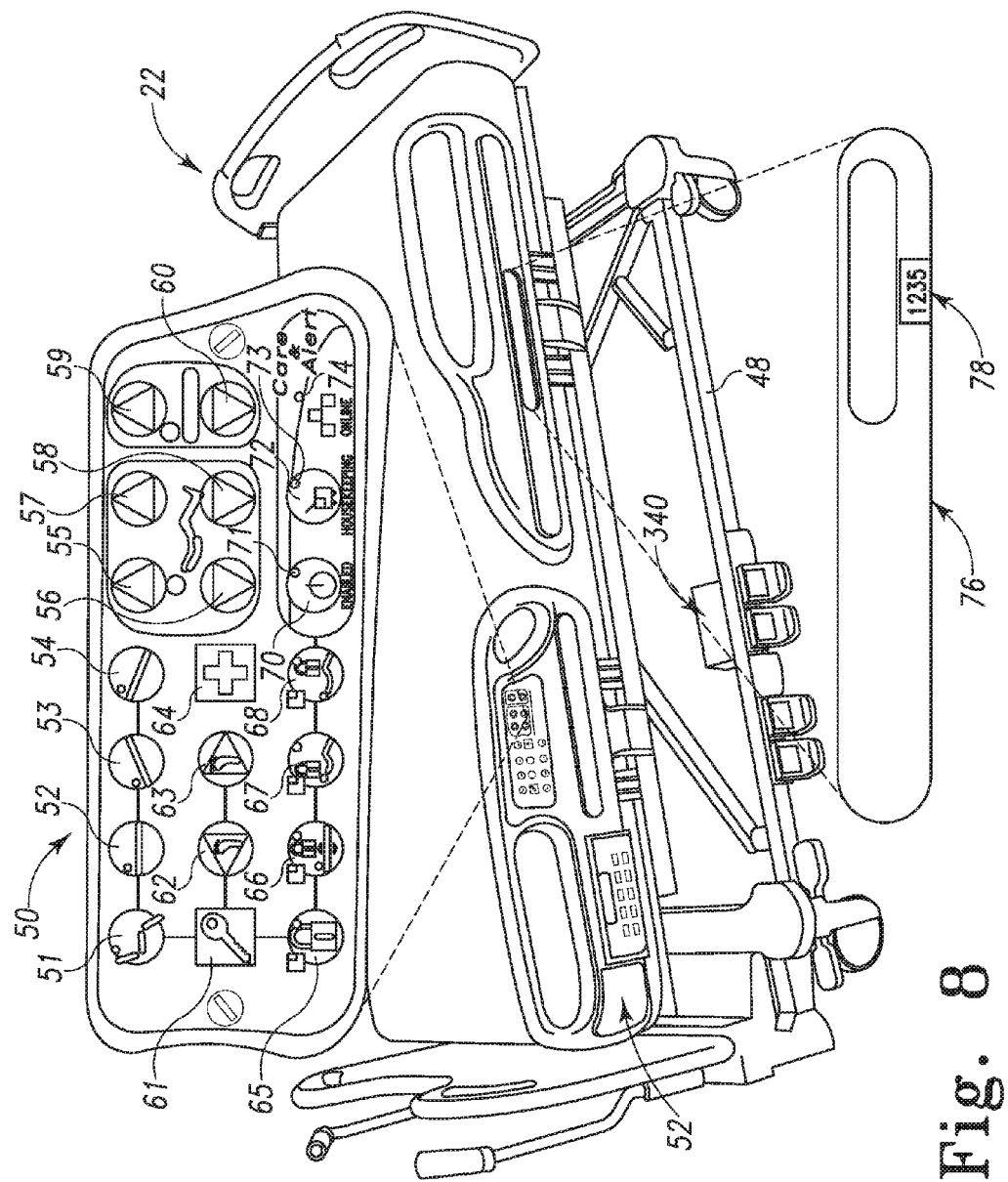
FIG. 8 is a perspective view of an embodiment of a hospital bed, with one enlarged portion of the view showing a user interface including LED's to indicate whether or not wireless communications are enabled, whether or not wireless communications are online, and whether or not housekeeping has been summoned to clean the associated bed and/or hospital room, and another enlarged portion of the view showing a label having bed ID data.

Referring now to FIG. 8, one embodiment of bed 22 (illustratively, a VersaCare™ bed marketed by Hill-Rom Company, Inc.) has an associated WCM 340 mounted to a base frame 48 of bed 22. Bed 22 of FIG. 8 also has a user interface 50 accessible on the outwardly facing side of a siderail 52 of bed 22. In FIG. 8, an enlarged view of user interface 50 is shown so the various indicia associated with various control buttons can bee seen more easily. Various buttons that are pressed to control associated functions of bed 22 are included on user interface 50. These buttons include the following: a chair button 51 to articulate a mattress support deck of the bed 22 into a chair position; a "go to flat" button 52 to move the mattress support deck into a flat position; a Trendelenburg button 53 to tilt the mattress support deck into a Trendelenburg position; a reverse Trendelenberg button 54 to tilt the mattress support deck into a reverse Trendelenburg position; a head up button 55 to pivot a head section of the mattress support deck upwardly, a head down button 56 to pivot the head section of the mattress support deck downwardly; a knee up button 57 to pivot a thigh section of the mattress support deck upwardly; a knee down button 58 to pivot the thigh section of the mattress support deck downwardly; a raise button 59 to raise the mattress support deck and an upper frame carrying the mattress support deck upwardly relative to base frame 48; a lower button 60 to lower the mattress support deck and the upper frame downwardly relative to base frame 48; a key button 61 that is pressed to enable the use of other buttons for certain bed functions; a foot retract button 62 to shorten a foot section of the mattress support deck; a foot extend button 63 to lengthen the foot section of the mattress support deck; a nurse call button 64 to place a nurse call to a remote nurse call computer; a lock button 65 that is pressed simultaneously with other buttons to lock or unlock certain bed functions; a hi/lo motor lockout button 66 to lock out hi/lo motors of bed 22 to prevent the upper frame and mattress support deck from being raised and lowered relative to base frame 48; a head motor lockout 67 to lock out a head section actuator from raising and lowering the head section of the mattress support deck; and a thigh motor lockout 68 to lock out a thigh section motor from raising and lowering a thigh section of the mattress support deck.

Bed 22 has a label 76 with bed ID data 78 thereon as shown in FIG. 8. In some embodiments, the bed ID data 78 is the MAC address assigned to bed 22. Additional details of bed 22 of FIG. 8 are shown and described in U.S. Pat. No.

6,957,461 and U.S. Patent Application Publication No. 2005/0172405 which are hereby incorporated by reference herein.

In connection with the wireless communication capability of bed 22 of FIG. 8, user interface 50 has an enabled button 70 with an indicator 71, a housekeeping button 72 with an indicator 73, and an on-line indicator 74. In some embodiments, indicators 71, 73, 74 are light emitting diodes (LED's), such as LED's that are operable to shine red, green, and/or amber. For example, when bed 22 is successfully wirelessly communicating with a wireless access point 42 of network, indicator 74 may shine green and when no wireless communications are taking place, indicator 74 may shine red. Indicator 74 may shine yellow during a time period in which bed 22 is attempting to reestablish wireless communication with network 20 after wireless communications are initially lost. In other embodiments, one or more of indicators 71, 73, 74 may comprise single color LED's.

Successive presses of enabled button 70 enable and suspend a Care Alert template for bed 22. Successive presses of housekeeping button 72 makes a housekeeping request and cancels the housekeeping request. However, in order for presses of buttons 70, 72 to be effective, key button 61 must first be pressed and held for a predetermined period of time, such as one second. Once button 61 has been pressed for the predetermined period of time, then buttons 70, 72 may be pressed within another predetermined period of time, such as 20 seconds, to change the state of the associated feature of buttons 70, 72. This control scheme for buttons 61, 70, 72 prevents inadvertent presses of buttons 70, 72 from changing the associated state of the associated feature. In some embodiments, indicator 71 of button 70 shines green when the Care Alert template associated with bed 22 is enabled, blinks or flashes green when the Care Alert template associated with bed 22 is suspended, and is turned off when no Care Alert template is set up for bed 22. In some embodiments, indicator 73 shines green when a housekeeping request has been made by a press of button 72 and is turned off when no housekeeping request has been made or after a housekeeping request has been canceled. The housekeeping request may be canceled before or after a staff member actually cleans the bed and/or room.

In the illustrative example, button 72 has thereon a mop and bucket icon which matches the appearance of a mop and bucket icon which is displayed on one or more display screens that are associated with the workflow software application of computer 38 to indicate that a housekeeping task has been assigned to a staff member of the healthcare facility. The mop and bucket icon is of the type used in the NaviCare® software marketed by Hill-Rom Company, Inc. Thus, button 72 may be pressed to indicate that bed 22 needs to be cleaned (e.g., its linen and/or bed sheets changed, sprayed with a disinfectant spray, wiped down with a disinfectant, etc.) or even that the room in which bed 22 is situated needs to be cleaned and/or readied for the next patient. Therefore, the bed status data transmitted from bed 22, either wirelessly via the associated WCM 340 or via the wired connection to an associated NIU 366, in response to button 72 being pressed includes housekeeping data that is destined for the workflow software application of computer 38 in the illustrative example.

Receipt by computer 38 of the housekeeping data indicating that the bed and/or room needs to cleaned results in the workflow software application of computer 38 automatically assigning a housekeeping task to a selected staff member. Computer 38 then displays the assigned task on various display screens with a mop and bucket icon and the assigned staff member's name (or other staff member ID). If the assigned staff member is carrying a portable wireless communication device, such as a pager or a Vocera™ badge, then computer 38 may also initiate a wireless message to the portable communication device of the assigned staff member in response to receipt of housekeeping data from bed 22. In some embodiments, after button 72 is pressed to send housekeeping data to system 40, button 72 may be pressed again to cancel the housekeeping request or to indicate that the housekeeping task has been completed as discussed above.

Figure 9A:
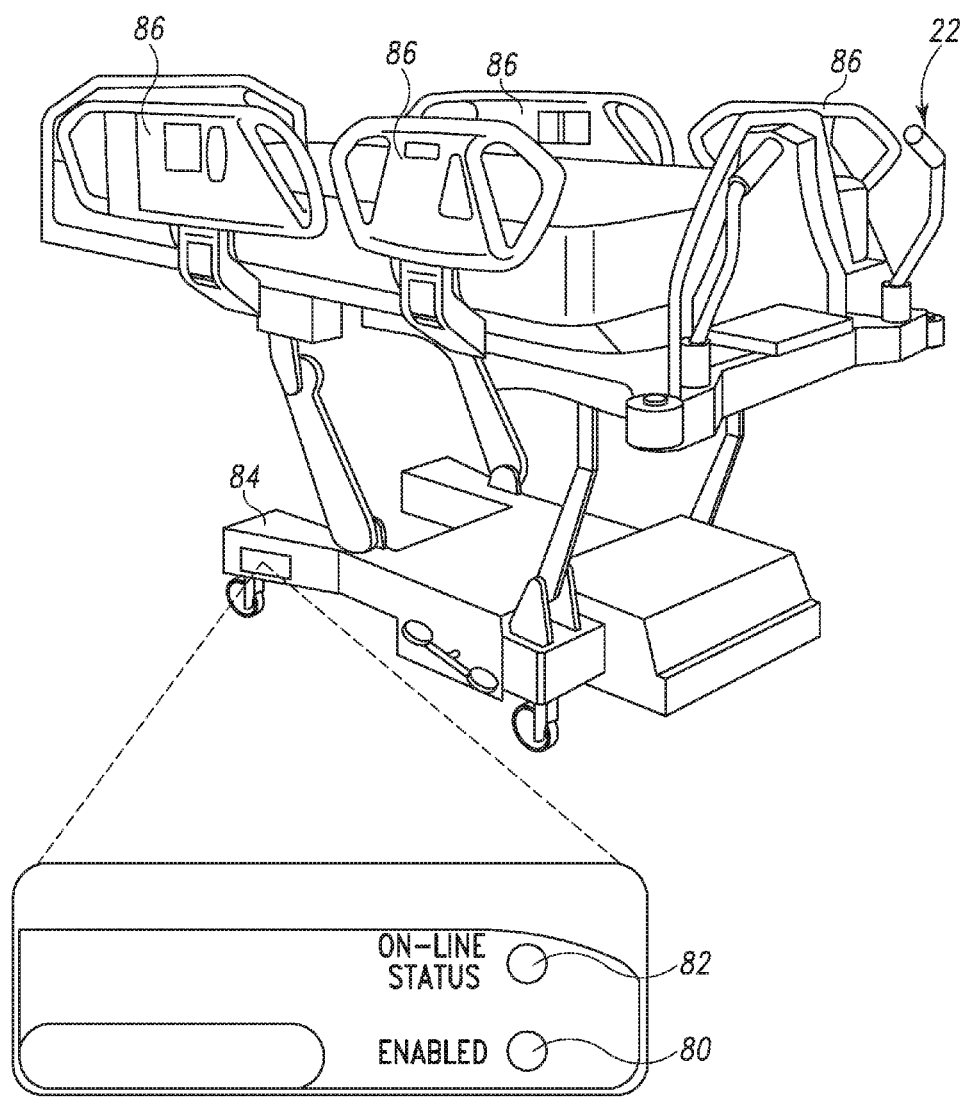
FIGS. 9A and 9B are perspective views of beds according to another embodiment, with one enlarged portion of the view associated with one of the beds showing indicator LED's on a base frame of the bed to indicate whether or not wireless communications are enabled and whether or not wireless communications are online, and another enlarged portion of the view associated with another of the beds showing a label having bed ID data and a bar code.
Figure 9B:
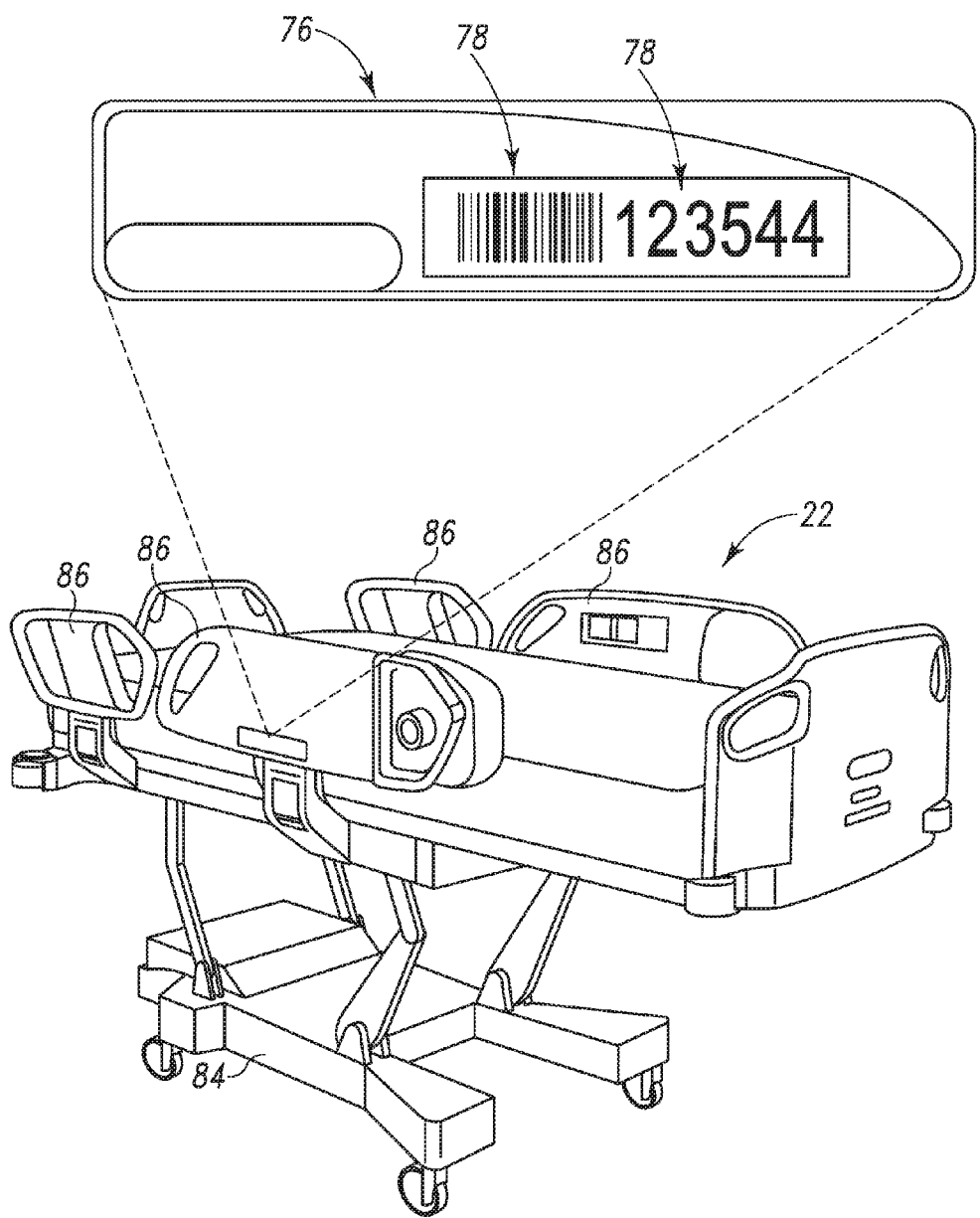

Referring now to FIG. 9, another embodiment of bed 22 (illustratively, a TotalCare® bed marketed by Hill-Rom Company, Inc.) includes an enabled indicator 80 and an on-line status indicator 82 on a base frame 84 of the bed 22. An enable button (not shown) is provided on one or more of siderails 86 of bed 22. Other than the fact that indicators 80, 82 are mounted to base frame 84 of the FIG. 9 bed 22, whereas indicators 71, 74 are mounted to siderail 52 of the FIG. 8 bed 22, indicators 80, 82 are substantially the same as indicators 71, 74 and therefore, the discussion above of indicators 71, 74 is equally applicable to indicators 80, 82. Optionally, the FIG. 9 bed 22 may also include a housekeeping button, with or without an associated housekeeping indicator, on one siderails 86 which functions in the same manner as button 72 (and indicator 73, if present) described above. Bed 22 of FIG. 9 also has a label 76 with bed ID data 78 thereon. Bed ID data includes numerical data and a bar code in the illustrative example of label 76 of the FIG. 9 bed. Label 76 is substantially the same as label 76 so the same reference numeral is used. In some embodiments, the bed ID data 78 is the MAC address assigned to the FIG. 9 bed 22. Additional details of bed 22 of FIG. 9 are shown and described in U.S. Pat. No. 5,715,548 which is hereby incorporated by reference herein.

Figure 10:
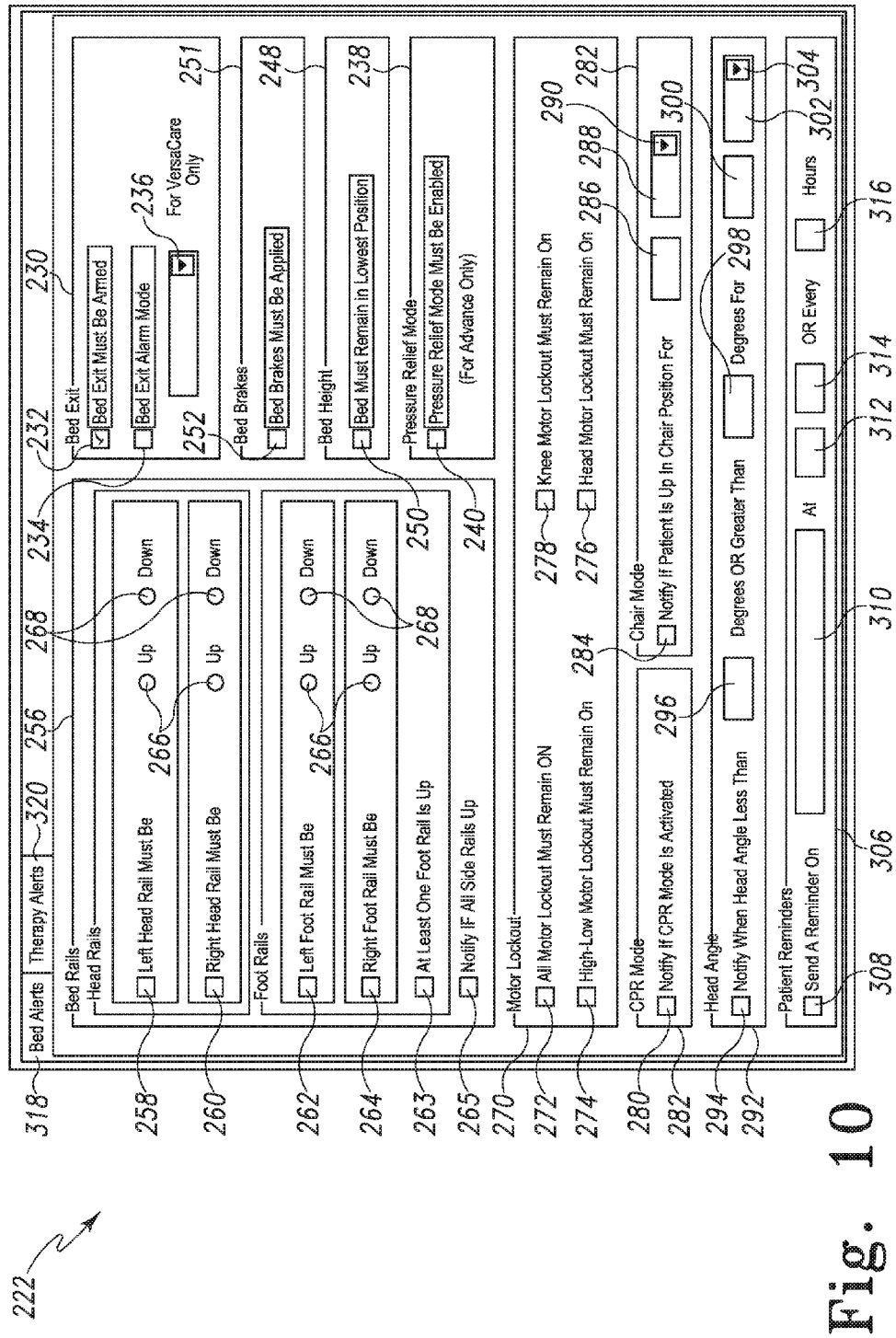
FIG. 10 is a screen shot of a bed alert template that appears on a display screen of a computer at a nurse call station and that has various check boxes, text boxes, and drop down menus for selection of alert parameters to which one or more caregivers are to be alerted.

FIG. 10 is a screen shot of a "Bed Alerts" template screen 222, which is another example of a Care Alert template (see the Care Alert template examples and discussion in U.S. patent application Ser. No. 11/189,781 which is already incorporated by reference herein), that appears on a display screen of computer 38 to enable a caregiver to select various alert conditions for an associated bed 22 to which one or more assigned. Screen 222 has configurable alert conditions associated with the bed status data received by computer 38 from the associated bed 22. Screen 222 has various check boxes and radio buttons that are selected in screen 222 to configure system 112 with the associated alert conditions. Screen also has various text boxes in which data is typed.

Screen 222 includes a Bed Rails window 256 which includes therein a Head Rails portion with a "Left head rail must be" check box 258 and a "Right head rail must be" check box 260. Window 256 also has a Foot Rails portion with a "Left foot rail must be" check box 262, and a "Right foot rail must be" check box 264. Beside each check box 258, 260, 262, 264 is an associated Up radio button 266 and an associated Down radio button 268. Window 256 also has an "At least one foot rail is up" check box 263 and a "Notify if all side rails up" check box 265. Thus, by appropriately checking boxes 258, 260, 262, 263, 264, 265 and appropriately selecting radio buttons 266, 268, computer 38 will automatically send a notification to one or more assigned caregivers when the associated condition is violated as indicated by bed status data received by computer 38.

Screen 22 has a Bed Exit window 230 with a "Bed exit must be armed" check box 232 and a "Bed exit alarm mode" check box 234. Window 230 also has a menu arrow icon 236 which is selected to cause a drop down menu of bed exit alarm mode options to appear. Screen 222 further has a Bed Height window 248 which includes therein a "Bed must remain in lowest position" check box 250 and a Bed Brakes window 251 which includes a "Bed brakes must be applied" check box 252. Screen has a "Pressure Relief Mode" window 238 with a "Pressure relief mode must be enabled" check box 240. Thus, by appropriately checking boxes 232, 234, 240, 250, 252 and appropriately entering data in box 236 (box 236 is only used for some bed some embodiments), computer 38 will automatically send a notification to one or more assigned caregivers if an associated condition is violated as indicated by bed status data received by computer 38.

Screen 222 also has a Motor Lock Out window 270 which includes therein an "All motor lockout must remain on" check box 272, a "High-Low motor lockout must remain on" check box 274, a "Head motor lockout must remain on" check box 276, and a "Knee motor lockout must remain on" check box 278. Thus, by appropriately checking boxes 272, 274, 276, 278, computer 38 will automatically send a notification to one or more assigned caregivers if an associated condition is violated as indicated by bed status data received by computer 38.

Screen 222 further has a CPR Mode window 280 with a "Notify if CPR mode is activated" check box 282. In addition, screen 222 has a Chair Mode window 282 with a "Notify if patient is up in chair position for" check box 284, a greater than/less than text box 286, and a time text box 288 with a drop down menu arrow icon 290. Screen 22 has a Head Angle window 292 with a "Notify when head angle less than" check box 294, a first angle text box 296, a second angle text box 298 (with the phrase "Degrees OR Greater Than" between boxes 294, 296), an hours text box 300, and a minutes text box 302 with a drop down menu arrow icon 304. Finally, screen 222 has a Patients reminders window 306 with a "Send reminder on" check box 308, an hours clock box 312, a minutes clock box 314, and an hours interval box 316. Thus, by appropriately checking boxes 282, 284, 294, 308 and appropriately entering data in boxes 286, 288,296, 298, 300, 302, 310, 312, 314, 316, computer 38 will automatically send a reminder to one or more assigned caregivers at the appropriate time when the associated condition is met.

Figure 11:
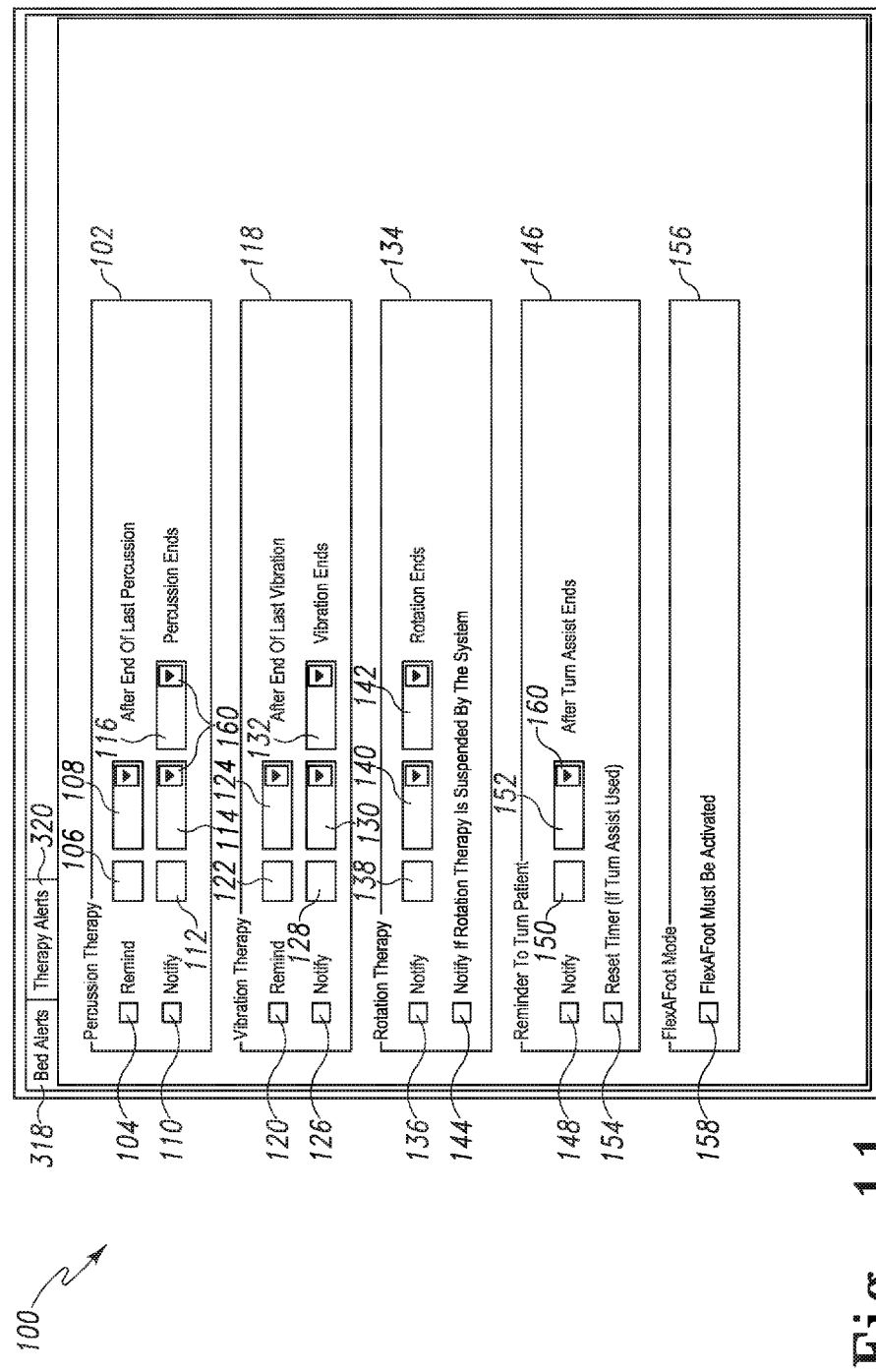
FIG. 11 is a screen shot of a therapy alert template that appears on a display screen of a computer at a nurse call station and that has various check boxes, text boxes, and drop down menus for selection of alert parameters to which one or more caregivers are to be alerted.

Across the top of screen 222 are tabs which are selectable to view an associated Care Alert template. For example, the bed alerts of FIG. 10 appear when a Bed Alerts tab 318 is selected. In the illustrative example, a Therapy Alerts tab 320 also appears on screen 222. Selection of tab 320 results in a Therapy Alerts screen 100 being displayed on the display screen of computer 38 as shown in FIG. 11. Screen 100 has a Percussion Therapy window 102 with a remind check box 104 adjacent to an hours text box 106 and a minutes text box 108. The phrase "After end of last percussion" appears to the right of box 108. Window 102 also has a notify check box 110 adjacent to an hours text box 112, minutes text box 114, and a before/after text box 116. The phrase "Percussion ends" appears to right of box 116. Thus, by appropriately checking boxes 104, 110 and appropriately entering data in boxes 106, 108, 112, 114, 116, computer 38 will automatically send a reminder to one or more assigned caregivers a predetermined period of time after the last percussion of a percussion therapy surface and/or will notify one or more assigned caregivers that percussion therapy will end within a predetermined time or has ended a predetermined period of time ago.

Screen 100 also has a Vibration Therapy window 118 with a remind check box 120 adjacent to an hours text box 122 and a minutes text box 124. The phrase "After end of last vibration" appears to the right of box 124. Window 118 also has a notify check box 126 adjacent to an hours text box 128, minutes text box 130, and a before/after text box 132. The phrase "Vibration ends" appears to the right of box 132. Thus, by appropriately checking boxes 120, 126 and appropriately entering data in boxes 122, 124, 128, 130, 132, computer 38 will automatically send a reminder to one or more assigned caregivers a predetermined period of time after the last vibration of a vibration therapy surface and/or will notify one or more assigned caregivers that vibration therapy will end within a predetermined time or has ended a predetermined period of time ago.

Screen 100 further has a Rotation Therapy window 134 with a notify check box 136 adjacent to an hours text box 138, minutes text box 140, and a before/after text box 142. The phrase "Rotation ends" appears to the right of box 142. Thus, by checking boxes 136 and appropriately entering data in boxes 138, 140, 142, computer 38 will automatically notify one or more assigned caregivers that rotation therapy will end within a predetermined time or has ended a predetermined period of time ago. Window 134 also has a "Notify if rotation therapy is suspended by the system" check box 144. When box 144 is checked, computer 38 automatically notifies a caregiver if rotation therapy stops, such as may occur, for example, if a siderail of bed 22 is lowered during rotation therapy.

Additionally, screen 100 has a Reminder to Turn Patient window 146 with a notify check box 148 adjacent to an hours text box 150 and a minutes text box 152. The phrase "After turn assist ends" appears to the right of box 152. Thus, by checking box 148 and appropriately entering data in boxes 150, 152, computer 38 will automatically notify one or more assigned caregivers that turn assist has ended a predetermined period of time ago. Window 146 also has a Reset Timer (If Turn Assist Used) check box 154. If box 154 is checked, then computer 38 will automatically reset a timer back to the start of the predetermined period entered in boxes 150, 152. Screen 100 has a FlexAFoot Mode window 156 with a FlexAFoot Must Be Activated check box 158. FlexAFoot is a bed feature that permits extension and retraction of a foot section of bed 22. Thus, when box 158 is checked, bed 22 must be in a mode that permits extension and retraction of the foot section (e.g., the extension and retraction feature of the foot section should not be locked out). Several of the text boxes of screen 100 have drop down menu arrow icons 160 which, when selected, cause an appropriate menu, such as a minutes menu (listing 00-60) or a before/after menu to appear on screen 100.

As discussed above, when various ones of the alert conditions, remind conditions, or notify conditions (hereinafter referred to collectively as "alert conditions") selected on screens 100, 222 are met, computer 38 transmits a message to one or more assigned caregivers. According to this disclosure such messages regarding alert conditions are transmitted wirelessly to portable wireless communication devices carried by the one or more caregivers. The following are exemplary of the types of wireless communications initiated by computer 38 in response to data received by computer 38 from bed 22 and/or surface 46 matching one or more of the alert conditions selected on one or more of the Care Alert templates of screens 100, 222: paging a pager (with or without an associated text message indicating the alert condition and patient room number); sending a selected preprogrammed audio message to caregivers who are carrying voice communication badges (such as Vocera™ badges) or handsets (such as Spectralink™ handsets or Ascom™ handsets); sending a text message to voice communication badges, handsets, or other wireless communication devices (PDA's, cell phones, etc.) having text messaging capability; and sending a preprogrammed audio message to an audio station at the location where an assigned caregiver is determined to be by locating-and-tracking software of computer 38.

Based on the foregoing, it will be appreciated that when an alert condition occurs, computer 38 operates to notify one or more caregivers of the alert condition automatically via a page and/or text message and/or audio message. Thus, no caregiver at a master nurse station, for example, needs to take any further action to notify assigned caregivers of alert conditions. A database of computer 38 stores information about the types of wireless communication devices carried by each of the caregivers and computer 38 operates to initiate the appropriate type of wireless communication based on the particular type of wireless communication device carried by the associated caregiver.

According to this disclosure, when any of beds 22 connect to network 20, computer 38 receives configuration data from the bed 22 which indicates the firmware version stored in memory of bed 22. Computer 38 stores the latest version of bed firmware for various models of beds, which bed firmware on computer 38 may be sent to computer 38 by the bed manufacturer via the Internet or installed on computer 38 on site. Computer 38 compares the firmware version indicated by the configuration data with the latest version stored in computer 38. If the configuration data indicates that the bed 22 does not have the latest version of firmware installed, then computer 38 automatically downloads the latest version of firmware to bed 22. FIGS. 12-16 show a state diagram and flow charts that illustrate this process. Additional details of bed programming is described in Appendix 5 which was attached to U.S. Provisional Application No. 60/773,286 which already is incorporated by reference herein and which will be accessible via the USPTO website when the present application is published.

Figure 12:
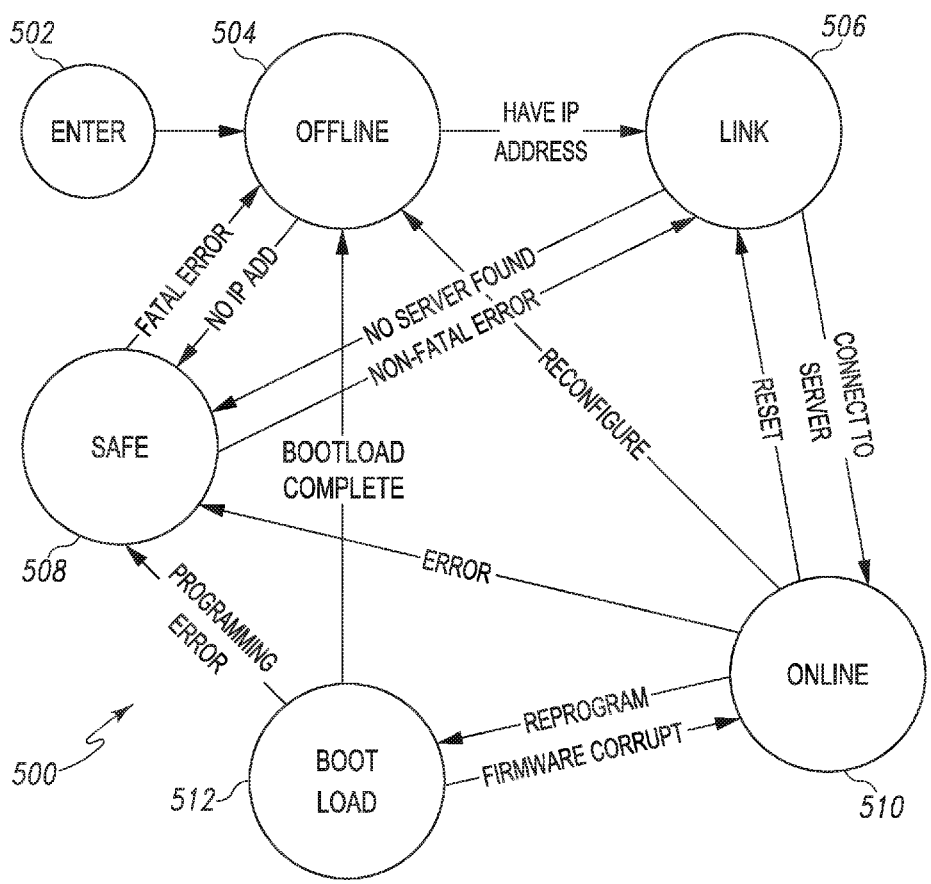
FIG. 12 is a state machine transition diagram showing how offline, link, safe, boot load, and online modes are logically interconnected.

A state diagram 500 of the firmware download algorithm of bed 22 includes an enter point 502, an offline mode 504, a link mode 506, a safe mode 508, an online mode 510 and a boot load mode 512 as shown in FIG. 12. Enter point 502 indicates that the algorithm starts in offline mode 504 which logically proceeds to link mode 506 if bed 22 has an IP address or which logically proceeds to safe mode 508 if bed 22 does not receive an IP address. From link mode 506, the algorithm logically proceeds to safe mode if bed 22 is unable to communicate with server 38 or logically proceeds to online mode 510 if bed 22 is able to communicate with server 38. From safe mode 508, the algorithm logically proceeds to offline mode 504 is a fatal error is detected or logically proceeds to link mode 506 if no fatal error is detected. From online mode 510, the algorithm logically proceeds to boot load mode 512 if the firm ware of bed 22 needs to be reprogrammed, logically proceeds to offline mode 504 if bed 22 needs to be configured with an IP address, logically proceeds to link mode 506 if bed 22 receives a reset command, or logically proceeds to safe mode 508 is an error is detected. From boot load mode 512, the algorithm logically proceeds to offline mode 504 if bed 22 successfully downloads the new firmware, logically proceeds to safe mode 508 is a programming error is detected, or logically proceeds to online mode 510 if firmware corruption is detected.

Figure 13:
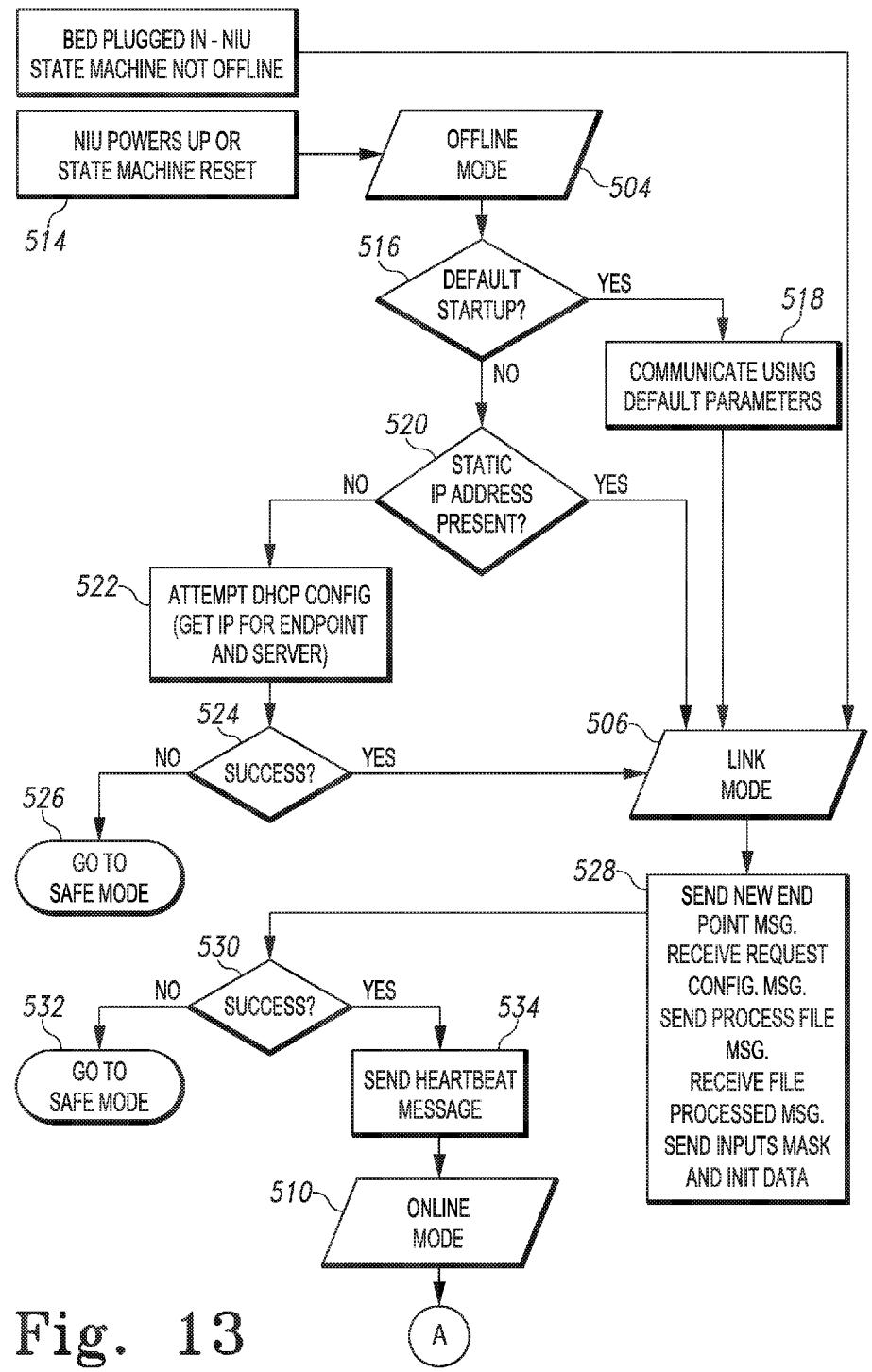
FIGS. 13-16 are flow charts which together show, in more detail, the logic of a software algorithm of a wireless hospital bed in accordance with the state machine transition diagram of FIG. 12.

Referring now to FIG. 13, if NIU 366 powers up or a state machine reset is received, the algorithm proceeds to offline mode 504 as indicated at block 514. In the offline mode 504, bed 22 determines whether a default startup has occurred as indicated at block 516. If a default startup has occurred, then bed 22 communicates using default parameters as indicated at block 518 and proceeds to link mode 506. If a default startup has not occurred, then bed 22 determines whether a static IP address is present as indicated at block 520. If a static IP address is present, then bed 22 proceeds to link mode 506. If a static IP address is not present, then bed 22 attempts a DHCP configuration to get an IP address for the bed 22 and/or server 38 as indicated at block 522. At block 524, bed 22 determines whether the attempt of block 522 was successful. If the attempt at block 524 was not successful, bed 22 proceeds to safe mode 508 as indicated at block 526. If the attempt at block 524 was successful, bed 22 proceeds to link mode 506. Bed 22 also enters link mode 506 if the bed 22 is plugged in and the NIU is not offline.

Still referring to FIG. 13, after entering link mode 506, bed 22 sends a new end point message, receives a request configuration message, sends a process file message, receives a file processed message, and sends an inputs mask and initial data message as indicated at block 528. At block 530, bed 22 determines whether all of the messages associated with block 528 were successfully sent or received, as the case may be. If all of the messages at block 528 were not successfully sent or received, then bed proceeds to safe mode 508 as indicated at block 532. If all of the messages at block 528 were successfully sent and received, then bed 22 sends a heartbeat message as indicated at block 534 and proceeds to online mode 510. According to this disclosure, the heartbeat message sent by bed 22 has the format "Copyright © Bed Manufacturer Year" (e.g. Copyright © Hill-Rom 2006).

Figure 14:
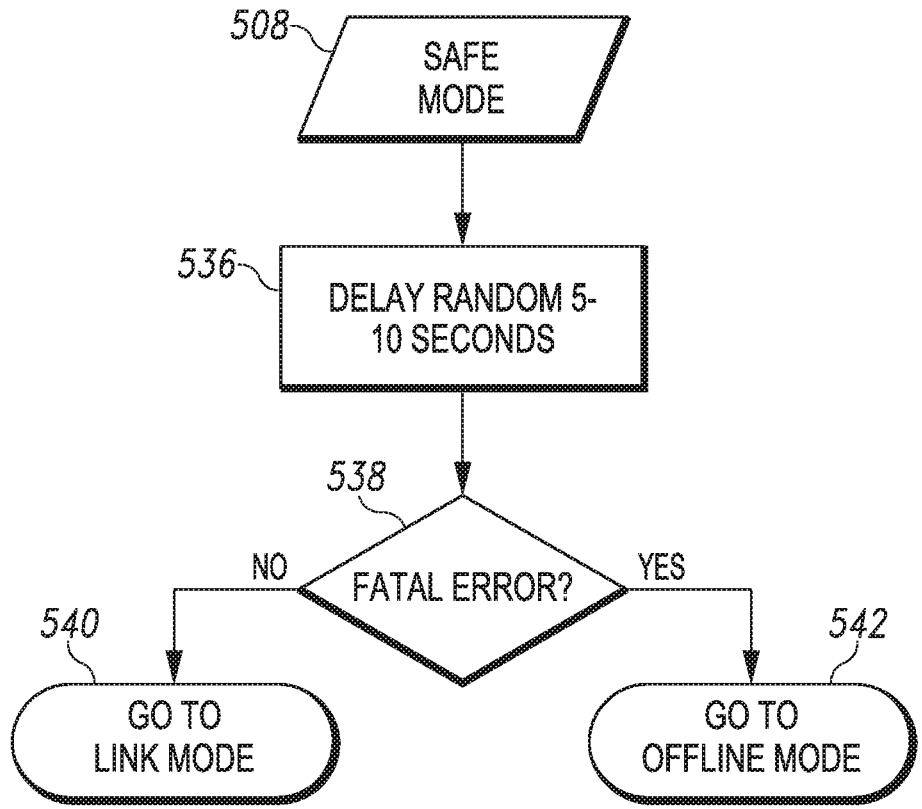

If bed 22 enters safe mode 508, either at block 526 or block 532 of FIG. 13, then bed 22 will delay further algorithm execution for a randomly established period of 5 to 10 seconds as indicated at block 536 shown in FIG. 14 and then proceed to determine whether a fatal error has occurred as indicated at block 538 shown in FIG. 14. If a fatal error has not occurred, then bed 22 will proceed to link mode 506 as indicated at block 540. If a fatal error has occurred, then bed 22 will proceed to offline mode 504 as indicated at block 542.

Figure 15:
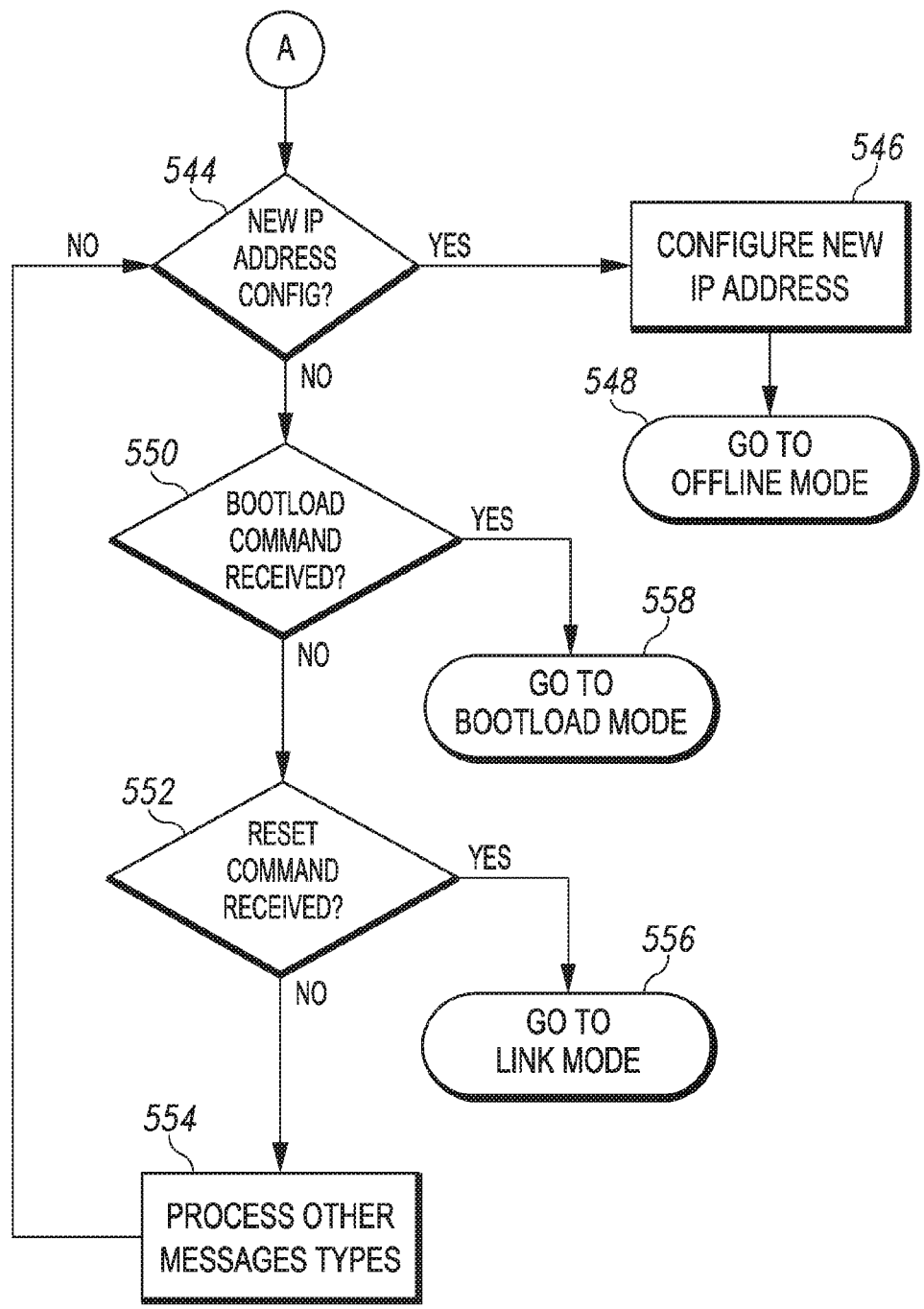

If bed 22 enters online mode 510 from block 534 in FIG. 13, then bed 22 determines whether a new IP address needs to be configured as indicated at block 544 shown in FIG. 15. If a new IP address does need to be configured, then bed 22 communicates with network 20 to configure a new IP address as indicated at block 546 and then proceeds to offline mode 504 as indicated at block 548. If no IP address needs to be configured at block 544, then bed 22 determines whether a boot load command has been received as indicated at block 550. If no boot load command has been received at block 550, bed 22 determines whether a reset command has been received as indicated at block 552. If no reset command has been received at block 552, then bed 22 process other types of messages as indicated at block 554 and loops back to block 544. If a reset command has been received at block 552, then bed 22 proceeds to link mode 506 as indicated at block 556. If a boot load command has been received at block 550, then bed 22 proceeds to boot load mode 512 as indicated at block 558.

Figure 16:
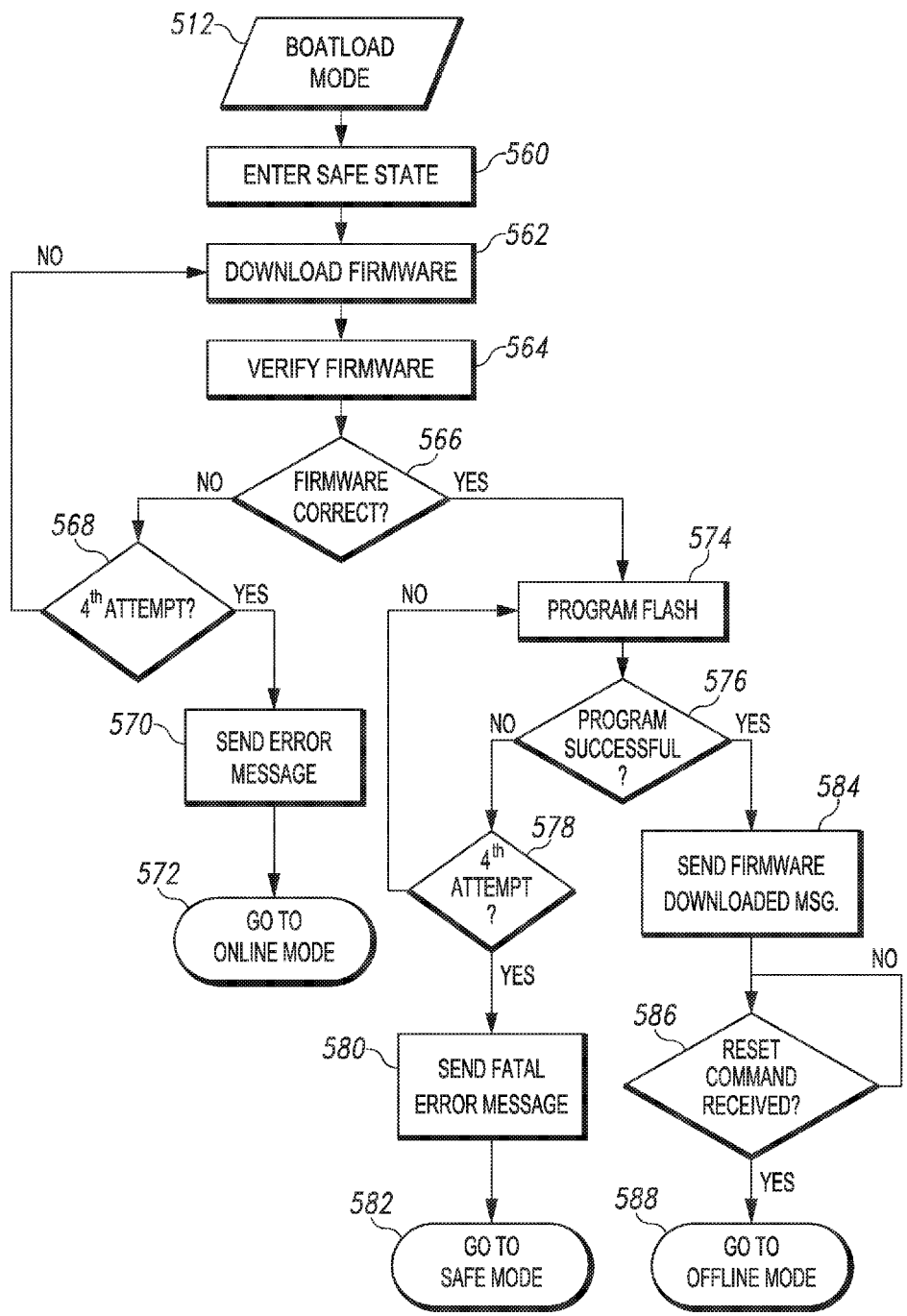

Referring to FIG. 16, after bed 22 enters boot load mode 512, bed 22 enters a safe state as indicated at block 560, downloads firmware from server 38 as indicated at block 562, and verifies the firmware as indicated at block 564. Bed 22 then proceeds to determine whether the firmware is correct as indicated at block 566. If the firmware is not correct, bed 22 determines whether a fourth attempt to determine if the firmware is correct has been made as indicated at block 568. If the attempt to determine if the firmware is correct is not the fourth attempt, then bed 22 loops back to block 562 and executes the steps of blocks 562, 564, 566 once again. If the attempt to determine if the firm is correct is the fourth attempt, bed 22 sends an error message to server 38 as indicated at block 570 and proceeds to online mode 510 as indicated at block 572.

If bed 22 determines that the firmware is correct at block 566, bed 22 programs the firmware into flash memory of bed 22 as indicated at block 574 and then determines whether the flash memory was successfully programmed with the new firmware as indicated at block 576. If the flash memory was not successfully programmed, bed 22 determines whether a fourth attempt to program the flash memory has been made as indicated at block 578. If the attempt to program the flash memory is not the fourth attempt, then bed 22 loops back to block 574 to make another attempt to program the new firmware into the flash memory. If the attempt to program the flash memory is the fourth attempt at block 578, then bed 22 sends a fatal error message to server 38 as indicated at block 580 and proceeds to safe mode 508 as indicated at block 582. If the flash memory was successfully programmed at block 576, bed 22 sends a firmware-downloaded message as indicated at block 584 and proceeds to determine whether a reset command has been received from server 38 as indicated at block 586. Bed 586 waits in a continuous loop at block 586 until a reset command is received from server 38 and then, once the reset command is received, bed 22 proceeds to offline mode 504 as indicated at block 588.

Although certain embodiments have been described in detail above, variations and modifications exist within the scope and spirit of this disclosure as described and as defined in the following claims.

The invention claimed is:

1. An interface unit for use in a healthcare facility having a computer located remotely from a patient room which has a patient bed therein, the interface unit being located in the patient room and spaced from the patient bed, the interface unit comprising:
a first connector which is communicatively coupleable to the hospital bed,
a second connector which is communicatively coupleable to the computer, and
circuitry comprising at least two device connectors for connection to external devices, the circuitry storing a unit identification (ID) that is associated with the patient room of the healthcare facility, the unit ID being transmitted by the circuitry through the second connector without transmitting the unit ID through the first connector and the at least two device connectors.

2. The interface unit of claim 1, wherein at least one device connector of the at least two device connectors comprises an Ethernet port for connection of the circuitry to an Ethernet of the healthcare facility.

3. The interface unit of claim 2, wherein the Ethernet port comprises an RJ-45 port.

4. The interface unit of claim 2, wherein the data from the hospital bed is received by the circuitry via the first connector according to a first communication protocol and the circuitry converts the data from the first protocol into an Ethernet protocol.

5. The interface unit of claim 4, wherein the data from the hospital bed is sent to the computer via the second connector according to the first protocol.

6. The interface unit of claim 1, wherein the data from the hospital bed is passed through to the computer via the first and second connectors.

7. The interface unit of claim 6, wherein the data from the hospital bed that is passed through to the computer includes a nurse call signal.

8. The interface unit of claim 6, wherein the data from the hospital bed that is passed through to the computer includes a signal for controlling room lighting.

9. The interface unit of claim 6, wherein the data from the hospital bed that is passed through to the computer includes a signal for controlling entertainment.

10. The interface unit of claim 1, wherein at least one device connector of the at least two device connectors comprises a JTAG connector.

11. The interface unit of claim 1, wherein the first connector is communicatively coupled to the hospital bed via a wired data link.

12. The interface unit of claim 1, wherein the first connector is communicatively coupled to the hospital bed via a wireless data link.

13. The interface unit of claim 1, wherein the second connector is communicatively coupled to the computer via a wired data link.

14. The interface unit of claim 1, wherein the second connector is communicatively coupled to the computer via a wireless data link.

15. The interface unit of claim 1, wherein at least one device connector of the at least two device connectors comprises at least one general purpose input/output (GPIO) connector.

16. The interface unit of claim 1, wherein the at least two device connectors comprises at least two general purpose input/output (GPIO) connectors.

17. The interface unit of claim 1, wherein at least one device connector of the at least two device connector comprises a serial peripheral interface (SPI) connector.

18. The interface unit of claim 1, wherein the at least two device connectors comprises multiple general purpose input/output (GPIO) connectors and a serial peripheral interface (SPI) connector.

19. The interface unit of claim 18, wherein the at least two device connectors further comprises a JTAG connector.

20. The interface unit of claim 18, wherein the at least two device connectors further comprises an RJ-45 port.

* * * * *